(12) United States Patent
Noda et al.

(10) Patent No.: US 9,233,185 B2
(45) Date of Patent: Jan. 12, 2016

(54) ABSORBENT ARTICLE

(71) Applicant: UNICHARM CORPORATION, Shikokuchuo (JP)

(72) Inventors: Yuki Noda, Kanonji (JP); Tatsuya Tamura, Kanonji (JP); Akira Hashino, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 14/389,256

(22) PCT Filed: Mar. 26, 2013

(86) PCT No.: PCT/JP2013/058859
§ 371 (c)(1),
(2) Date: Sep. 29, 2014

(87) PCT Pub. No.: WO2013/146817
PCT Pub. Date: Oct. 3, 2013

(65) Prior Publication Data
US 2015/0051566 A1 Feb. 19, 2015

(30) Foreign Application Priority Data

Mar. 30, 2012 (JP) ................................. 2012-080539

(51) Int. Cl.
*A61F 13/15* (2006.01)
*A61L 15/46* (2006.01)
(Continued)

(52) U.S. Cl.
CPC ............. *A61L 15/46* (2013.01); *A61F 13/4704* (2013.01); *A61F 13/47218* (2013.01);
(Continued)

(58) Field of Classification Search
CPC ........... A61F 13/15203; A61F 13/4704; A61F 13/4756; A61F 13/47218; A61F 13/47227; A61F 13/51104; A61F 13/51108; A61F 13/8405; A61F 2013/15284; A61F 2013/15292; A61F 2013/15317; A61F 2013/15357; A61F 2013/15373; A61F 2013/15406; A61F 2013/8438

See application file for complete search history.

(56) References Cited

U.S. PATENT DOCUMENTS 3,929,135 A 12/1975 Thompson
(Continued)

FOREIGN PATENT DOCUMENTS

CN 1432352 A 7/2003
EP 1250940 A1 10/2002
(Continued)

OTHER PUBLICATIONS

Atsushi Fujita, "Prediction of Organic Compounds and Organic Conceptual Diagram", Kagaku no Ryoiki (Region of Chemistry), Oct. 1957, p. 719-725, vol. 11, No. 10.
(Continued)

*Primary Examiner* — Lynne Anderson
(74) *Attorney, Agent, or Firm* — Hauptman Ham, LLP

(57) ABSTRACT

The purpose of the present disclosure is to provide an absorbent article that can be made smaller because the crown section continues to fit the wearer's excretory opening, which has a complex shape, both when dry before absorbing menstrual blood and when wet after absorbing menstrual blood, and with which leakage does not occur easily. This absorbent article is as follows: The absorbent article (1), which comprises a liquid-permeable top sheet (4), a liquid-impermeable back sheet, and a specified absorbent (7) between the liquid permeable top sheet (4) and the liquid-impermeable back sheet, is characterized in that: the absorbent article (1) has a crown section (2), which protrudes in the thickness direction of the absorbent article (1) in the region that is in contact with the excretory opening and comprises a specified cushion section; and in the central section, the crown section (2) has a compression workload (WC) of 10-50 (N·m/m$^2$) and a compression resilience (RC) of 35-100%.

14 Claims, 10 Drawing Sheets

(51) Int. Cl.

| | | |
|---|---|---|
| *A61F 13/511* | (2006.01) | |
| *A61F 13/47* | (2006.01) | |
| *A61F 13/472* | (2006.01) | |
| *A61F 13/535* | (2006.01) | |
| *A61F 13/515* | (2006.01) | |
| *A61L 15/28* | (2006.01) | |
| *A61L 15/60* | (2006.01) | |
| *A61F 13/51* | (2006.01) | |

(52) U.S. Cl.
CPC ........ *A61F 13/47227* (2013.01); *A61F 13/515* (2013.01); *A61F 13/51104* (2013.01); *A61F 13/535* (2013.01); *A61L 15/28* (2013.01); *A61L 15/60* (2013.01); *A61F 2013/15292* (2013.01); *A61F 2013/15406* (2013.01); *A61F 2013/5108* (2013.01)

(56) References Cited

U.S. PATENT DOCUMENTS

| | | |
|---|---|---|
| 4,588,630 A | 5/1986 | Shimalla |
| 4,759,754 A | 7/1988 | Korpman |
| 5,078,710 A | 1/1992 | Suda et al. |
| 5,334,176 A | 8/1994 | Buenger et al. |
| 5,344,416 A | 9/1994 | Niihara |
| 5,614,283 A | 3/1997 | Potnis et al. |
| 5,650,214 A | 7/1997 | Anderson et al. |
| 6,153,209 A | 11/2000 | Vega et al. |
| 6,210,385 B1 * | 4/2001 | Mizutani ............ A61F 13/15203 604/385.01 |
| 6,326,525 B1 * | 12/2001 | Hamajima ............ A61F 13/4752 604/378 |
| 6,730,819 B1 | 5/2004 | Pesce |
| 7,279,613 B2 * | 10/2007 | Nozaki ............ A61F 13/15203 604/379 |
| 2001/0029141 A1 | 10/2001 | Mizutani et al. |
| 2003/0088222 A1 | 5/2003 | Yoshimasa et al. |
| 2003/0149410 A1 | 8/2003 | Kudo et al. |
| 2003/0198784 A1 | 10/2003 | Mizutani et al. |
| 2005/0124951 A1* | 6/2005 | Kudo ................ A61F 13/47218 604/380 |
| 2006/0184150 A1 | 8/2006 | Noel |
| 2006/0189954 A1* | 8/2006 | Kudo ................ A61F 13/15203 604/380 |
| 2006/0276767 A1 | 12/2006 | Ueminami et al. |
| 2007/0219515 A1 | 9/2007 | Marsh et al. |
| 2007/0298213 A1 | 12/2007 | Noda et al. |
| 2007/0298214 A1 | 12/2007 | Noda et al. |
| 2007/0298220 A1 | 12/2007 | Noda et al. |
| 2007/0298667 A1 | 12/2007 | Noda et al. |
| 2007/0298671 A1 | 12/2007 | Noda et al. |
| 2007/0299416 A1 | 12/2007 | Noda et al. |
| 2008/0010795 A1 | 1/2008 | Mizutani et al. |
| 2008/0044622 A1 | 2/2008 | Noda et al. |
| 2008/0044628 A1 | 2/2008 | Noda et al. |
| 2008/0045915 A1 | 2/2008 | Noda et al. |
| 2008/0085399 A1 | 4/2008 | Noda et al. |
| 2008/0132136 A1 | 6/2008 | Uematsu et al. |
| 2008/0200894 A1 | 8/2008 | Gatto et al. |
| 2009/0221978 A1 | 9/2009 | Gatto et al. |
| 2009/0282660 A1 | 11/2009 | Noda et al. |
| 2010/0069874 A1 | 3/2010 | Noda et al. |
| 2010/0137824 A1 | 6/2010 | Uematsu et al. |
| 2010/0191207 A1 | 7/2010 | Oba et al. |
| 2011/0130737 A1* | 6/2011 | Sagisaka ............ A61F 13/4704 604/380 |
| 2011/0319851 A1 | 12/2011 | Kudo et al. |
| 2012/0045620 A1 | 2/2012 | Oba et al. |
| 2012/0141742 A1 | 6/2012 | Yamaguchi et al. |
| 2012/0177889 A1 | 7/2012 | Uematsu et al. |
| 2012/0196091 A1 | 8/2012 | Mizutani et al. |
| 2012/0209233 A1* | 8/2012 | Steffen .................... A61L 15/24 604/370 |
| 2013/0034686 A1 | 2/2013 | Mitsuno |
| 2013/0137328 A1 | 5/2013 | Mitsuno |
| 2013/0143020 A1* | 6/2013 | Wood et al. ........... A61F 13/026 428/220 |
| 2013/0226123 A1 | 8/2013 | Kudo et al. |

FOREIGN PATENT DOCUMENTS

| | | |
|---|---|---|
| EP | 1362568 | 11/2003 |
| EP | 1371379 A1 | 12/2003 |
| EP | 2036521 A1 | 3/2009 |
| EP | 2409673 A1 | 1/2012 |
| EP | 2433602 A1 | 3/2012 |
| GB | 2262235 | 6/1993 |
| JP | S57-17081 | 4/1982 |
| JP | S64-34365 | 2/1989 |
| JP | S64-56051 | 3/1989 |
| JP | H01-158954 | 6/1989 |
| JP | 02152920 A | 6/1990 |
| JP | H02-229255 | 9/1990 |
| JP | H05-154176 | 6/1993 |
| JP | H06-5614 | 1/1994 |
| JP | 6502104 A | 3/1994 |
| JP | H07-84697 | 9/1995 |
| JP | H08-510665 | 11/1996 |
| JP | H08-322879 | 12/1996 |
| JP | H10-95810 | 4/1998 |
| JP | H10-510743 | 10/1998 |
| JP | H11-512643 | 11/1999 |
| JP | 2000-510376 | 8/2000 |
| JP | 3091283 | 9/2000 |
| JP | 2000-512886 | 10/2000 |
| JP | 2001-095845 | 4/2001 |
| JP | 2001-129019 | 5/2001 |
| JP | 2001-328191 | 11/2001 |
| JP | 2002-508693 | 3/2002 |
| JP | 3262172 | 3/2002 |
| JP | 2002528174 A | 9/2002 |
| JP | 2002537904 A | 11/2002 |
| JP | 200324372 A | 1/2003 |
| JP | 200352750 A | 2/2003 |
| JP | 2004-500908 | 1/2004 |
| JP | 200449529 A | 2/2004 |
| JP | 2005-504591 | 2/2005 |
| JP | 2005-095759 | 4/2005 |
| JP | 2005193001 A | 7/2005 |
| JP | 2005-525134 | 8/2005 |
| JP | 2006501022 A | 1/2006 |
| JP | 2006-510456 | 3/2006 |
| JP | 2006115996 A | 5/2006 |
| JP | 2006-255051 | 9/2006 |
| JP | 2006280526 A | 10/2006 |
| JP | 200714705 A | 1/2007 |
| JP | 2007-509695 | 4/2007 |
| JP | 2008-002034 | 1/2008 |
| JP | 2008-023311 | 2/2008 |
| JP | 2008-025080 | 2/2008 |
| JP | 2008-025081 | 2/2008 |
| JP | 2008-025082 | 2/2008 |
| JP | 2008-025083 | 2/2008 |
| JP | 2008-025084 | 2/2008 |
| JP | 2008-025085 | 2/2008 |
| JP | 2008-029830 | 2/2008 |
| JP | 2008-503323 | 2/2008 |
| JP | 200823365 A | 2/2008 |
| JP | 200825078 A | 2/2008 |
| JP | 200825079 A | 2/2008 |
| JP | 200829830 A | 2/2008 |
| JP | 2008-138340 | 6/2008 |
| JP | 2008-144322 | 6/2008 |
| JP | 2008-529721 A | 8/2008 |
| JP | 2008229032 A | 10/2008 |
| JP | 2008229033 A | 10/2008 |
| JP | 2008237569 A | 10/2008 |
| JP | 2008-264084 | 11/2008 |
| JP | 2008-266813 | 11/2008 |
| JP | 2008-541943 | 11/2008 |
| JP | 2008-307179 | 12/2008 |
| JP | 20095767 A | 1/2009 |
| JP | 2009-030218 | 2/2009 |

(56) References Cited

FOREIGN PATENT DOCUMENTS

| | | |
|---|---|---|
| JP | 2009-201878 | 9/2009 |
| JP | 2009297048 A | 12/2009 |
| JP | 201088822 A | 4/2010 |
| JP | 2010518918 A | 6/2010 |
| JP | 2010-148708 | 7/2010 |
| JP | 2010526629 A | 8/2010 |
| JP | 2010-285735 | 12/2010 |
| JP | 2010279568 A | 12/2010 |
| JP | 2011-038211 | 2/2011 |
| JP | 2011-074515 | 4/2011 |
| JP | 2011-080178 | 4/2011 |
| JP | 201167484 A | 4/2011 |
| JP | 201172650 A | 4/2011 |
| JP | 2011510801 A | 4/2011 |
| JP | 4693847 | 6/2011 |
| JP | 2011104001 A | 6/2011 |
| JP | 2011104059 A | 6/2011 |
| JP | 2011120696 A | 6/2011 |
| JP | 2011226010 A | 11/2011 |
| JP | 2011226011 A | 11/2011 |
| JP | 2012-050626 | 3/2012 |
| JP | 5122007 | 1/2013 |
| WO | 9301781 A1 | 2/1993 |
| WO | 94/27539 | 12/1994 |
| WO | 95/31165 A1 | 11/1995 |
| WO | 96/19173 | 6/1996 |
| WO | 98/55158 | 12/1998 |
| WO | 99/00093 | 1/1999 |
| WO | 99/29274 | 6/1999 |
| WO | 0024351 A1 | 5/2000 |
| WO | 00/63487 A1 | 10/2000 |
| WO | 01/45757 | 6/2001 |
| WO | 03/017900 | 3/2003 |
| WO | 03/028776 | 4/2003 |
| WO | 2004030713 A1 | 4/2004 |
| WO | 2004/058119 | 7/2004 |
| WO | 2005/044164 | 5/2005 |
| WO | 2006/009996 | 1/2006 |
| WO | 2006-130646 | 12/2006 |
| WO | 2008072675 A1 | 6/2008 |
| WO | 2008101163 A2 | 8/2008 |
| WO | 2008139425 A1 | 11/2008 |
| WO | 2008/149771 | 12/2008 |
| WO | 2009102837 A2 | 8/2009 |
| WO | 2012/133724 | 10/2012 |

OTHER PUBLICATIONS

International Search Report mailed Jul. 3, 2012 in corresponding International Application No. PCT/JP2012/058499.
International Search Report mailed Mar. 19, 2013 in corresponding International Application No. PCT/JP2012/082087.
International Search Report mailed Mar. 12, 2013 in corresponding International Application No. PCT/JP2012/082104.
International Search Report mailed Mar. 19, 2013 in corresponding International Application No. PCT/JP2013/054382.
International Search Report mailed May 21, 2014 in corresponding International Application No. PCT/JP2013/054796.
International Search Report mailed Jul. 2, 2013 in corresponding International Application No. PCT/JP2013/058860.
International Search Report mailed Jul. 2, 2013 in corresponding International Application No. PCT/JP2013/058861.
International Search Report mailed Jul. 2, 2013 in corresponding International Application No. PCT/JP2013/058862.
International Search Report mailed May 14, 2013 in corresponding International Application No. PCT/JP2013/058836.
International Search Report mailed Mar. 26, 2013, corresponds to International Application No. PCT/JP2012/082977.
International Search Report mailed Jan. 8, 2013, corresponds to International Application No. PCT/JP2012/075583.
International Search Report mailed Jul. 17, 2012, corresponds to International Application No. PCT/JP2012/061505.
Corresponding International Application No. PCT/JP2012/058499 Written Opinion dated Jul. 3, 2012.
Corresponding International Application No. PCT/JP2012/058499 Reply to Written Opinion dated Jan. 30, 2013.
International Search Report mailed May 21, 2013, corresponds to International Application No. PCT/JP2013/058859.
International Search Report mailed Jun. 18, 2013, corresponds to International Application No. PCT/JP2013/058855.

* cited by examiner

Fig.6
(a)
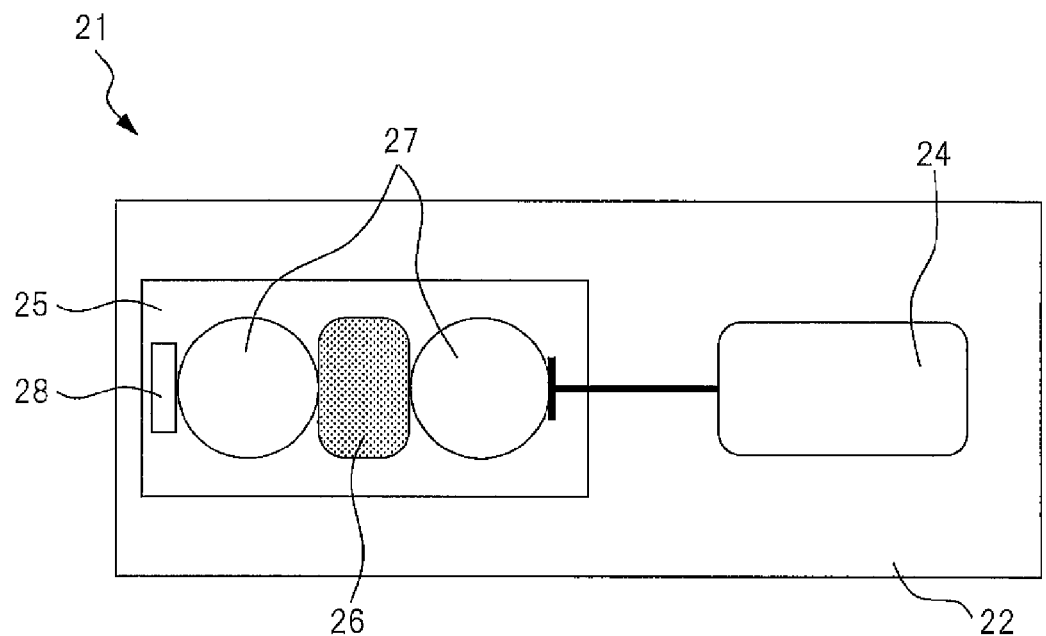
(b)
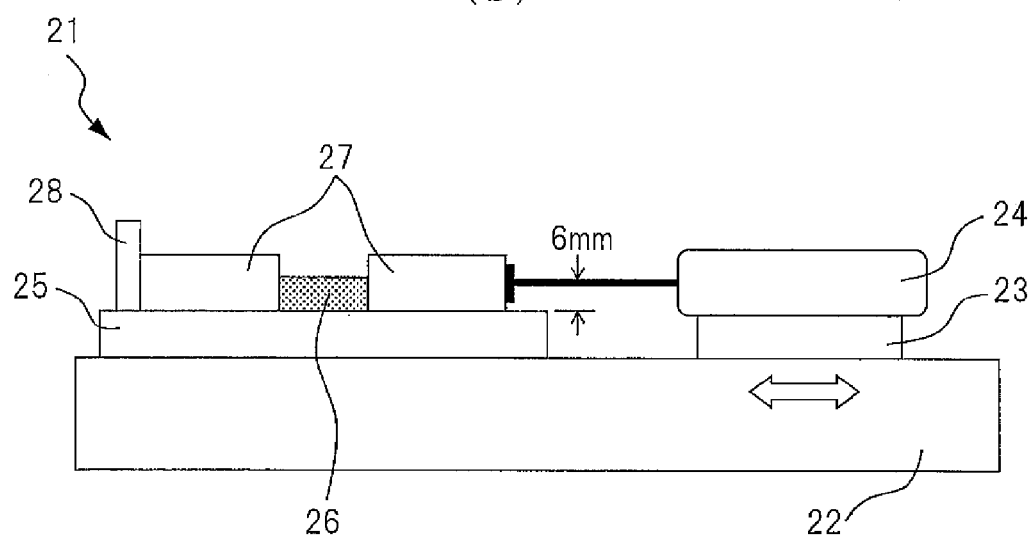

Fig.9
(a)
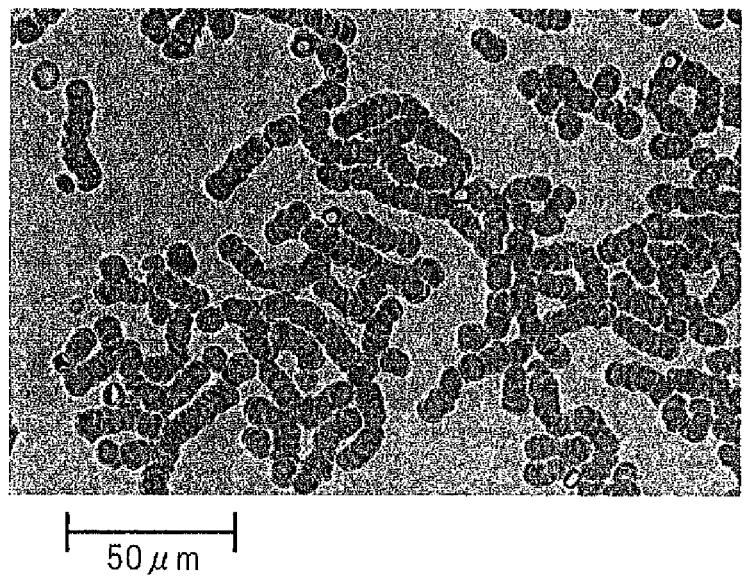
50 μm
(b)
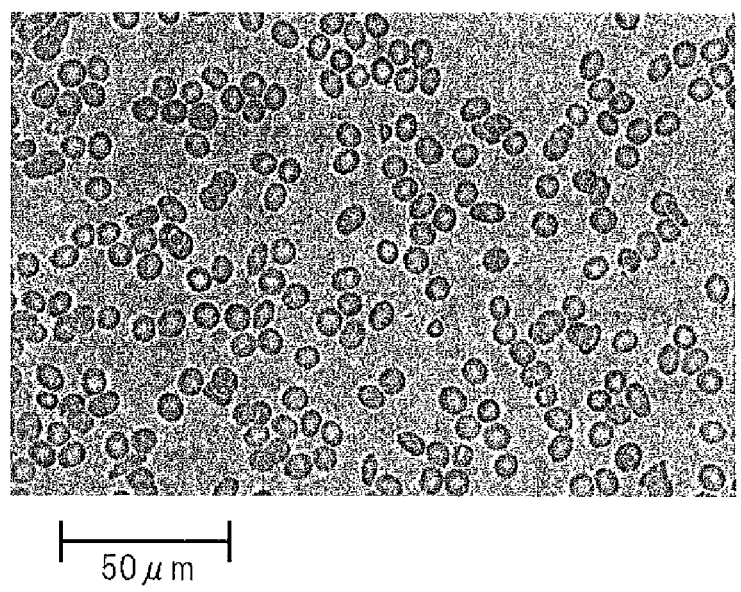
50 μm

ABSORBENT ARTICLE

CROSS-REFERENCES TO RELATED APPLICATIONS

The present application is National Phase of International Application Number PCT/JP2013/058859 filed Mar. 26, 2013 and claims the priority of Japanese patent Application No. 2012-080539 filed Mar. 30, 2012.

TECHNICAL FIELD

The present invention relates to an absorbent article.

BACKGROUND ART

Absorbent articles, such as sanitary napkins are known that have protrusions exhibiting cushioning properties on the skin contact surface of the top sheet, for suitable fitting with the body of the wearer. Having protrusions on the skin contact surface of the top sheet allows the protrusions to more suitably fit the body of the wearer to help prevent fluid leakage even when the body of the wearer has moved.

PTL 1, for example, describes an absorbent article designed to provide an absorbent article with excellent leakproofness and a satisfactory feel during wear.

The absorbent article described in PTL 1 is an essentially longitudinal absorbent article having the following structure: a liquid-impermeable leakproof layer and a liquid-retaining absorbing layer situated on the skin contact side from the leakproof layer, the absorbent article bending inward toward the skin contact side in the lengthwise direction, and having a neck section wherein the sides of the location corresponding to the excretion section narrow in width in the center direction as viewed flat, while having a convex curved surface protruding to the skin contact side on both sides in the lengthwise direction.

In paragraph [0013] of PTL 1 it is stated that the three-dimensional shape is preferably a center rising absorber 7 made of an absorbing member, and more specifically, that it is formed from pulp or the like.

CITATION LIST

Patent Literature

PTL 1 Japanese Unexamined Patent Publication No. 2000-33987

SUMMARY OF INVENTION

Technical Problem

In the absorbent article described in PTL 1, however, the rising section with a convex curved surface contains pulp, and therefore the bulk decreases when menstrual blood is absorbed during wear, and when compressive force is applied from the widthwise direction, the absorbent article excessively deforms into a protruding shape toward the skin of the wearer, causing shifting of the absorbent article and resulting in leakage of menstrual blood and a feeling of discomfort during wear.

It is therefore an object of the present disclosure to provide an absorbent article wherein the domed section continues to fit the complex-shaped excretory opening of the wearer both during periods of dryness before absorption of menstrual blood and during periods of wetness after menstrual blood has been absorbed, and therefore inhibits leakage, and therefore is reduced in size.

Solution to Problems

As a result of diligent research directed toward solving the problems described above, the present inventors have discovered an absorbent article comprising a liquid-permeable top sheet, a liquid-impermeable back sheet and an absorbent body between the liquid-permeable top sheet and liquid-impermeable back sheet, the absorbent article having in the excretory opening contact region a domed section that protrudes in the thickness direction of the absorbent article, the domed section including part of the top sheet and a cushion section disposed between the top sheet and the absorbent body, and having a center section and an outer peripheral section surrounding the center section, wherein the cushion section has a maximum thickness of 3 to 30 mm, the domed section has a work of compression WC of 10-50 (N·m/m²) and a compressional resilience RC of 35-100% at the center section, and the absorbent body has a length of 80 to 230 mm in the lengthwise direction of the absorbent article and a length of 30 to 90 mm in the widthwise direction of the absorbent article.

Advantageous Effects of Invention

The absorbent article of the present disclosure can be reduced in size because the domed section continues to fit the complex-shaped excretory opening of the wearer, and inhibits leakage, both during periods of dryness before absorption of menstrual blood and during periods of wetness after menstrual blood has been absorbed.

BRIEF DESCRIPTION OF DRAWINGS

FIG. 6 is a schematic diagram showing an example of an apparatus for measurement of compressive force.

FIG. 9 is a pair of photomicrographs of menstrual blood containing and not containing a blood modifying agent.

DESCRIPTION OF EMBODIMENTS

The absorbent article of the present disclosure will now be explained in detail.

Figure 1:
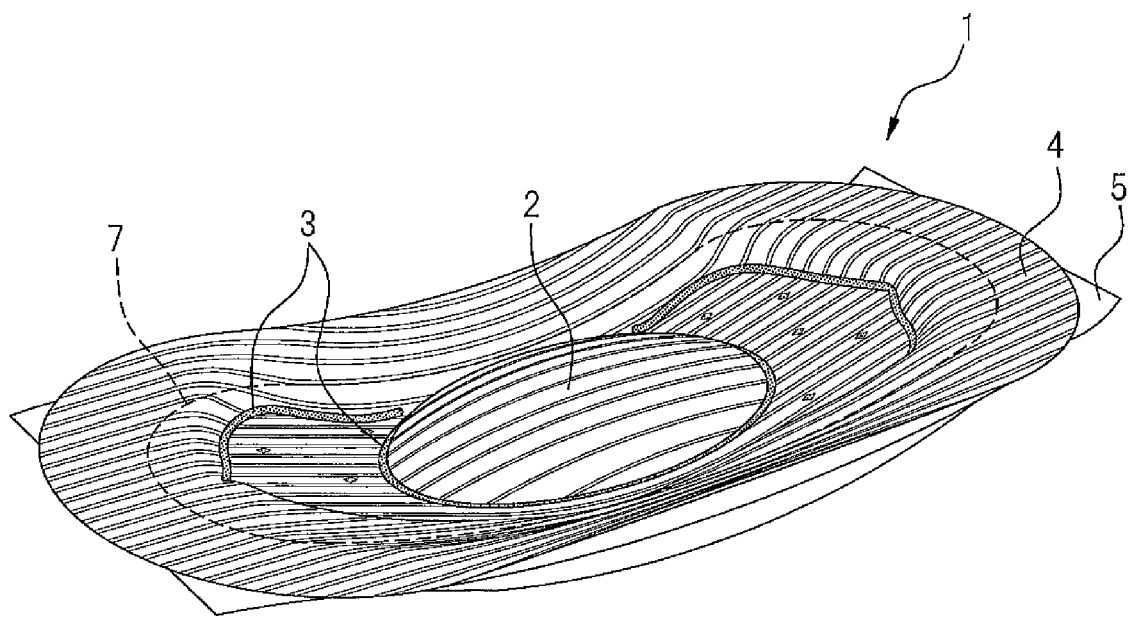
FIG. 1 is a perspective view of an absorbent article according to an embodiment of the present disclosure.

FIGS. 1 to 5 are views of an absorbent article according to an embodiment of the present disclosure. FIG. 1 is a perspective view of an absorbent article according to an embodiment of the present disclosure. The absorbent article 1 shown in FIG. 1 is a sanitary napkin. In the absorbent article 1 shown in FIG. 1, the right side corresponds to the front of the wearer while the left side corresponds to the back of the wearer, and the absorbent article 1 shown in FIG. 1 has a shape with essentially longitudinal symmetry and bilateral symmetry.

The absorbent article 1 shown in FIG. 1 comprises a liquid-permeable top sheet 4, a liquid-impermeable back sheet (not shown), and an absorbent body 7 between the liquid-permeable top sheet 4 and liquid-impermeable back sheet. Also shown in FIG. 1 are embossed sections 3, and a detaching portion 5 anchored to the back sheet.

The absorbent article 1 shown in FIG. 1 has a domed section 2 that protrudes in the thickness direction of the absorbent article 1 in the excretory opening contact region.

In the absorbent article 1 shown in FIG. 1, the top sheet 4 has a plurality of ridge-furrow structures extending in the lengthwise direction on the skin contact surface, the borders between the ridges and furrows being illustrated as solid lines for convenience in FIG. 1. In the absorbent article 1 shown in FIG. 1, the wide regions surrounded by two solid lines are the ridges and the narrow regions surrounded by two solid lines are the furrows, and in the absorbent article 1 shown in FIG. 1, a plurality of ridges and a plurality of furrows are alternately arranged in the widthwise direction of the absorbent article 1.

As used herein, the direction perpendicular to the lengthwise direction of the absorbent article will also be referred to as "widthwise direction".

Also as used herein, "domed section" refers to a section including part of the top sheet, and the cushion section, and in the domed section, the thickness generally decreases from the top part toward the outer edges.

Figure 2:
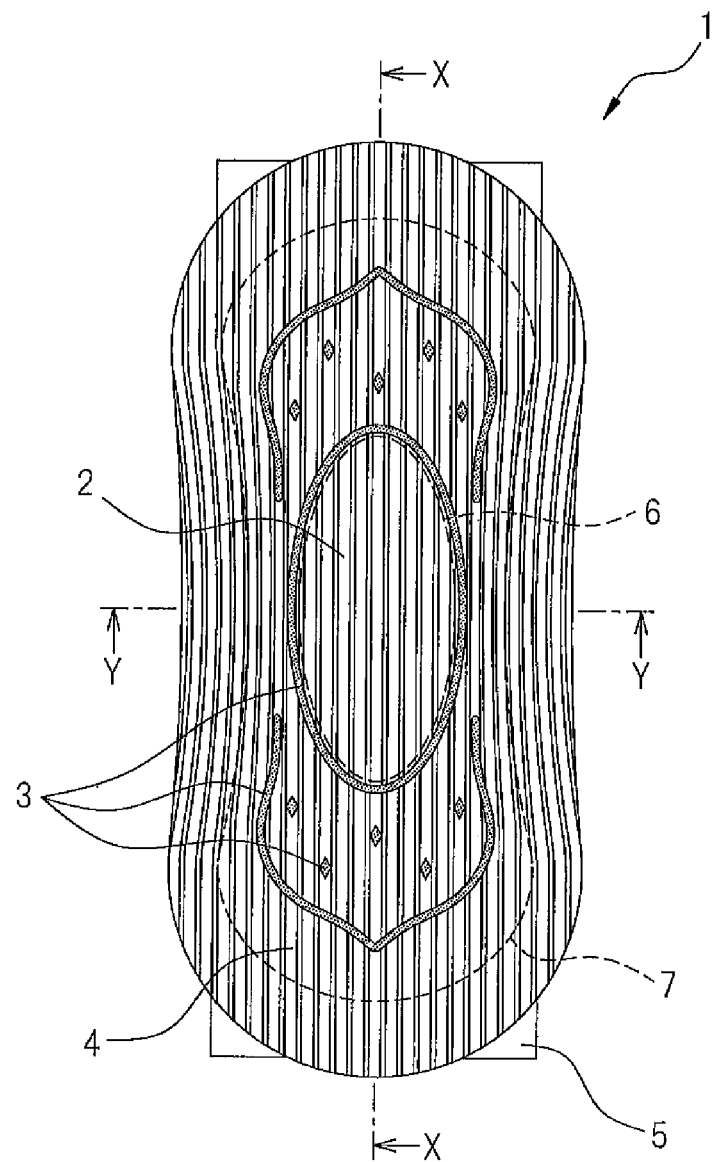
FIG. 2 is a front view of the absorbent article 1 shown in FIG. 1.

The "center section", as it relates to the domed section, is the region of preferably between 0 and about 50%, more preferably between 0 and about 40%, and even more preferably between 0 and about 30%, of the distance from the top part of the domed section to the outer edges of the domed section, in a front view of the absorbent article, such as shown in FIG. 2, while the remaining region is the "outer periphery" of the domed section.

FIG. 2 is a front view of the absorbent article 1 shown in FIG. 1, as observed from the skin contact side of the top sheet 4. In the absorbent article 1 shown in FIG. 2, the upper end corresponds to the front of the wearer, and the lower end corresponds to the back of the wearer. The absorbent article 1 shown in FIG. 2 comprises a liquid-permeable top sheet 4, a liquid-impermeable back sheet (not shown), and an absorbent body 7 between the liquid-permeable top sheet 4 and liquid-impermeable back sheet.

The absorbent article 1 shown in FIG. 2 also has a domed section 2 that protrudes in the thickness direction of the absorbent article 1 in the region in contact with the excretory opening contact region, and especially the labia minora. The domed section 2 includes part of the top sheet 4, and a cushion section 6 situated between the top sheet 4 and the absorbent body 7. Also shown in FIG. 2 are an embossed section 3, and a detaching portion 5 anchored to the back sheet.

Figure 3:
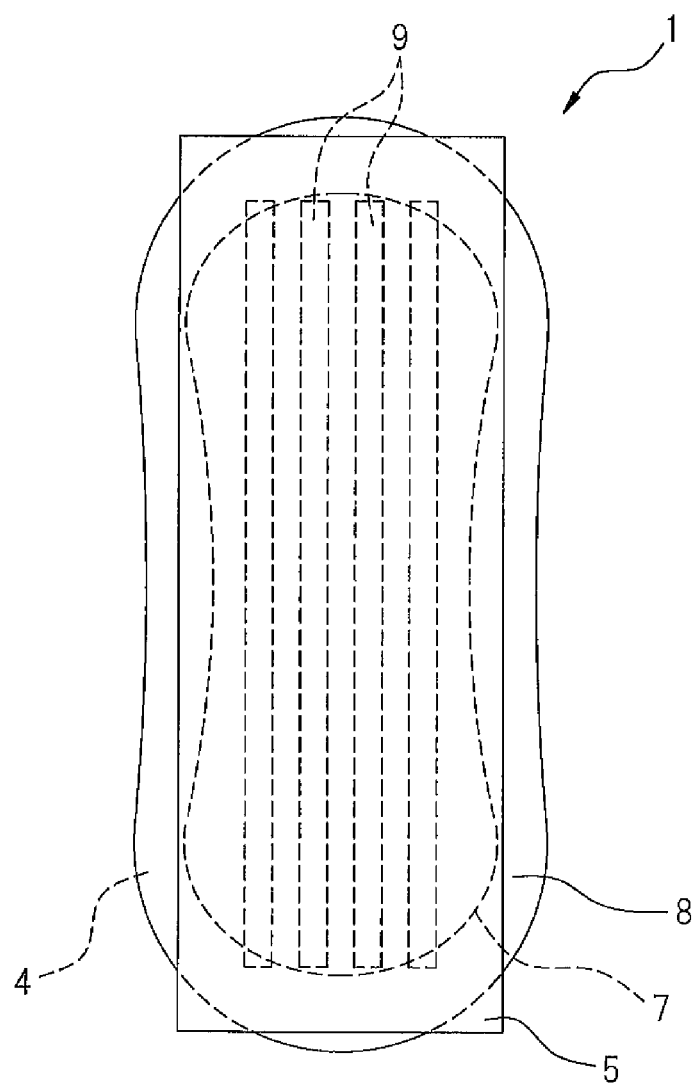
FIG. 3 is a rear view of the absorbent article 1 shown in FIG. 1.

FIG. 3 is a rear view of the absorbent article 1 shown in FIG. 1, as observed from the clothing contact surface side of the back sheet 8. In the absorbent article 1 shown in FIG. 3, the upper end corresponds to the front of the wearer, and the lower end corresponds to the back of the wearer. In the absorbent article 1 shown in FIG. 3, an anchoring part 9 is coated on the clothing contact surface of the liquid-impermeable back sheet 8, and the detaching portion 5 is temporarily anchored to the anchoring part 9. During use, the wearer may use the absorbent article 1 by detaching the detaching portion 5 from the anchoring part 9 and anchoring the anchoring part 9 to the clothing.

Figure 4:
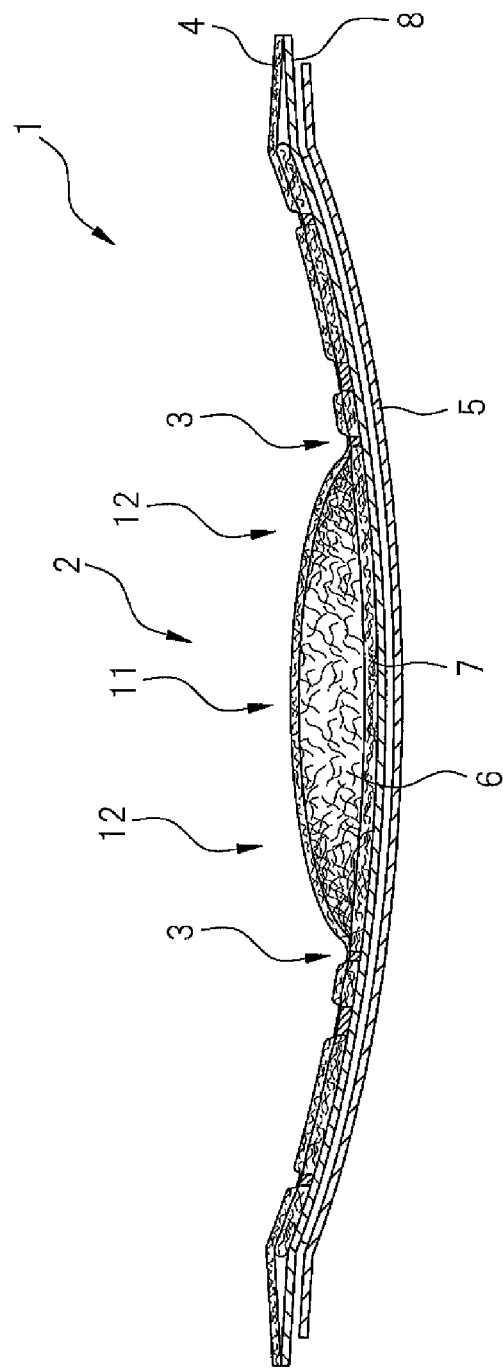
FIG. 4 is an end view of FIG. 2 along edge X-X.

FIG. 4 is an end view of FIG. 2 along edge X-X. In the absorbent article 1 shown in FIG. 4, a liquid-impermeable back sheet 8, absorbent body 7 and liquid-permeable top sheet 4 are layered in that order from the bottom, and a cushion section 6 is disposed between the absorbent body 7 and the liquid-permeable top sheet 4, in the excretory opening contact region.

Also, in the absorbent article 1 shown in FIG. 4, the domed section 2 includes part of the top sheet 4, and the cushion section 6, and the absorbent article 1 has an embossed section 3 formed by embossing the top sheet 4 and absorbent body 7 near the outer edge of the cushion section 6, and more specifically, outside the cushion section 6.

In the absorbent article 1 shown in FIG. 4, the cushion section 6 is formed from an air-through nonwoven fabric, and it has a maximum thickness of about 15 mm. The density of the cushion section 6 at the outer peripheral section 12, in the domed section 2 of the absorbent article 1 shown in FIG. 4, is higher than the density of the cushion section 6 at the center section 11.

Figure 5:
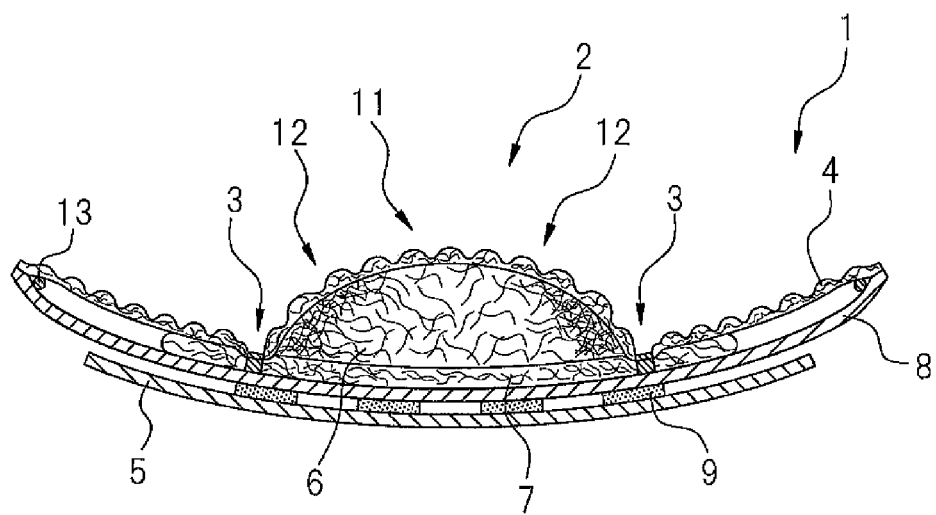
FIG. 5 is an end view of FIG. 2 along edge Y-Y.

FIG. 5 is an end view of FIG. 2 along edge Y-Y. The absorbent article 1 shown in FIG. 5 has an embossed section 3 formed by embossing the top sheet 4 and absorbent body 7 near the outer edge of the cushion section 6, and more specifically, outside the cushion section 6. In the absorbent article 1 shown in FIG. 5, the top sheet 4 has a plurality of ridge-furrow structures on the skin contact surface.

The density of the cushion section 6 at the outer peripheral section 12, in the domed section 2 of the absorbent article 1 shown in FIG. 5, is higher than the density of the cushion section 6 at the center section 11. An elastic member 13 is also shown in FIG. 5.

At the domed section 2 of the absorbent article 1 shown in FIG. 4 and FIG. 5, the density of the cushion section 6 at the outer peripheral section 12 is higher than the density of the cushion section 6 at the center section 11, but in an absorbent article according to a different embodiment of the present disclosure, the density of the cushion section at the outer peripheral section is identical to the density of the cushion section at the center section, while in an absorbent article according to yet another embodiment of the present disclosure, the density of the cushion section at the outer peripheral section is lower than the density of the cushion section at the center section.

The cushion section in the absorbent article is not particularly restricted, but preferably includes a nonwoven fabric in which the intersections of the fibers are heat fused. Examples of nonwoven fabrics in which the intersections of the fibers are heat fused include those that contain natural fibers, chemical fibers or both. Heat-fusing the fiber intersections provides excellent shape stability for the cushion section, and therefore the domed section, both during periods of dryness before absorption of menstrual blood and during periods of wetness after menstrual blood has been absorbed.

The nonwoven fabric in which the intersections between the fibers are heat-fused comprises approximately 50 to 100 mass % and more preferably approximately 70 to 100 mass % of thermoplastic chemical fibers, in order to accomplish heat fusion between the fibers.

The starting material for the thermoplastic chemical fibers may be polyethylene (PE), polypropylene (PP), polyethylene terephthalate (PET), PE and PP graft polymer, or the like, and examples of fiber types for the thermoplastic chemical fibers include single filaments, composite fibers, heat-shrinkable fibers, heat-extendable fibers, irregularly shaped fibers, solid crimped fibers and splittable fibers.

In consideration of facilitating uptake of menstrual blood and inhibiting rewet-back, the thermoplastic chemical fibers may be fibers comprising a hydrophilic agent, water-repellent agent or the like, or fibers coated with such an agent. Corona treatment or plasma treatment of the thermoplastic chemical fibers can result in hydrophilized fibers.

In order to increase the whiteness of the cushion section, the fibers may contain an inorganic filler, such as titanium oxide, barium sulfate or calcium carbonate. When the fibers composing the cushion section are core-sheath composite fibers, the core and/or sheath may contain the inorganic filler.

The fibers composing the cushion section are preferably composite fibers rather than single filaments, and more preferably core-sheath composite fibers comprising polyethylene in the sheath, from the viewpoint of compression recoverability of the domed section.

The composite fibers may be core-sheath composite fibers wherein the melting point of the core component is higher than the melting point of the sheath component, such as eccentric core-sheath composite fibers, or side-by-side composite fibers wherein the two components have different melting points. Also, irregularly shaped fibers include irregularly shaped fibers, such as hollow fibers, flat fibers, Y-shaped fibers or C-shaped fibers, solid crimped fibers include solid crimped fibers with latent crimping or developed crimping, and splittable fibers include splittable fibers that are split by a physical load, such as a water stream, heat, embossing or the like.

The fibers preferably have a size of about 1.1 to about 8.8 dtex, from the viewpoint of facilitating uptake of menstrual blood and improved feel on the skin.

Examples of natural fibers include cellulose, such as ground pulp or cotton, regenerated cellulose, such as rayon or fibril rayon, and semi-synthetic cellulose, such as acetate or triacetate, and combinations of the foregoing, with ground pulp being preferred from the viewpoint of low cost and easier shaping.

If the cushion section contains cellulose, regenerated cellulose and/or semi-synthetic cellulose, uptake of menstrual blood and leakage of menstrual blood is inhibited, when it is difficult to apply body pressure to the domed section, due to sleeping posture, etc. If the cushion section is composed of chemical fibers, such as a nonwoven fabric formed of 100% thermoplastic chemical fibers, menstrual blood will flow on the outer surface of the top sheet, potentially resulting in leakage.

The cushion section can be formed by web forming, in a dry system (carding method, spunbond method, meltblown method, airlaid method or TOW) or a wet system, or a combination thereof. The method for bonding the cushion section may be, for example, thermal bonding, needle punching, chemical bonding, hydroentangling or the like.

The cushion section is not particularly restricted, and for example, it is preferably an air-through nonwoven fabric, point bond nonwoven fabric, spunbond nonwoven fabric or spunbond/meltblown/spunbond nonwoven fabric (SMS nonwoven fabric) in which the fiber intersections are heat-fused, or a spunlace nonwoven fabric having heat fused intersections, but more preferably it includes an air-through nonwoven fabric. This is because an air-through nonwoven fabric has high bulk and low density, and excellent feel on the skin.

In the absorbent article of the present disclosure, the cushion section has a maximum thickness of about 3 to about 30 mm, preferably a maximum thickness of about 4 to about 20 mm, and more preferably a maximum thickness of about 5 to about 10 mm. If the maximum thickness of the cushion section is within this range, it will fit the excretory opening of the wearer, and especially the labia minora, during wearing, thus helping to reduce leakage.

The maximum thickness of the cushion section is the maximum thickness not of the cushion section removed from the absorbent article, but of the cushion section in the absorbent article.

In the absorbent article of the present disclosure, the domed section has a work of compression WC of about 10 to about 50 ($N \cdot m/m^2$), preferably a work of compression WC of about 15 to about 40 ($N \cdot m/m^2$) and more preferably a work of compression WC of about 20 to about 35 ($N \cdot m/m^2$), at the center section.

If the work of compression WC is less than about 10 ($N \cdot m/m^2$), the domed section will be resistant to compression, and therefore the labia minora will embed less easily in the domed section during wear, making it difficult for the domed section to be in continuous contact with the labia minora. If the work of compression WC is greater than about 50 ($N \cdot m/m^2$), the domed section will be compressed only by the weight of the menstrual blood, and a gap will form between the labia minora and the domed section, such that menstrual blood will tend to spread through the top sheet when menstrual blood has been repeatedly excreted.

In the absorbent article of the present disclosure, the domed section has a compressional resilience RC of about 35 to about 100%, preferably a compressional resilience RC of about 40 to about 100% and more preferably a compressional resilience RC of about 50 to about 100%, at the center section.

If the compressional resilience RC is less than about 35%, the bulk of the domed section will not promptly recover after absorption of menstrual blood when it is under body pressure from the wearer, such that it will be difficult for the domed section to be in continuous contact with the labia minora and a gap will be formed between the labia minora and the domed section, often resulting in leakage.

The work of compression WC is the value of the compressibility, i.e. the ease of compression, with a larger value indicating greater ease of compression. The compressional resilience RC is a value representing the recoverability of bulk after compression, and a value closer to 100% indicates higher recoverability.

Throughout the present specification, "compressibility" and "recoverability" may be collectively referred to as "compression recoverability".

If the domed section of the absorbent article of the present disclosure has a work of compression WC in the range specified above at the center section, the center section of the domed section will be able to continue to embed the labia minora of the wearer. Also, if the domed section has a compressional resilience RC in the range specified above at the center section, the bulk will promptly recover even when the domed section is temporarily collapsed (such as when body pressure is applied by the wearer or menstrual blood is excreted), and the center section of the domed section will embed the labia minora of the wearer, allowing continuous contact of the center section of the domed section with the labia minora.

The compressional resilience RC and work of compression WC are measured using a compression tester, such as a KES (Handy compression tester Model KES-G5) by Kato Tech Corp., for example.

When the value is to be measured using a KES-G5 by Kato Tech Corp. as the compression tester, the test conditions are set as follows.

Compression terminal area: 2.0 $cm^2$
Speed: 0.1 cm/sec
Maximum compressive force: 4900 $N/m^2$ In the absorbent article of the present disclosure, the domed section has a work of compression WC and compressional resilience RC within the aforementioned ranges at the center section, and therefore the domed section, and more specifically the cushion section, can promptly repeat compression and recovery, to provide a pump function that transports absorbed menstrual blood. That is, the cushion section can rapidly move absorbed menstrual blood into the absorbent body.

The cushion section in the absorbent article of the present disclosure has an average basis weight of preferably about 50 to about 1,000 g/m$^2$, more preferably about 100 to 500 g/m$^2$, and even more preferably about 150 to about 300 g/m$^2$. If the cushion section has an average basis weight within this range, the domed section will not collapse even during periods of wetness after menstrual blood has been absorbed, and the domed section will fit the excretory opening of the wearer, and especially the labia minora, thus reducing leakage.

The cushion section preferably has an average basis weight in the aforementioned range at the center section.

Throughout the present specification, "average basis weight" refers to the basis weight of the entire sample, obtained by dividing the weight of the sample (for example, cushion section or absorbent body) by the area.

In the absorbent article of the present disclosure, the cushion section has a compressive force of preferably about 0.1 to about 3.6N, more preferably about 0.2 to about 3.0N and even more preferably about 0.3 to about 2.0N.

It is known that when an absorbent article is compressed by the legs of a wearer during wear, it folds in the widthwise direction of the absorbent article and in such a manner that the skin contact surface of the top sheet protrudes outward (this will hereunder also be referred to as "outward deformation"), as the space decreases.

If the compressive force is less than about 0.1N, it may not be possible for the cushion section to undergo repulsion as the compression from the legs of the wearer has been relieved after the absorbent article has been deformed outward, so that the absorbent article can be rapidly restored to its original shape. If the compressive force is greater than about 3.6N, the repulsion of the cushion section will be excessively high, and it will tend to be difficult for the absorbent article to undergo outward deformation.

The compressive force may be measured in the following manner.

FIG. 6 is a schematic diagram showing an example of an apparatus for measurement of compressive force. FIG. 6(a) is a view from above the compressive force measuring apparatus 21, and FIG. 6(b) is a view from the side of the compressive force measuring apparatus 21. The compressive force measuring apparatus 21 shown in FIG. 6 has an operating stage 23 which is capable of left-right reciprocal movement, on a stand 22, a digital force gauge 24 which measures compressive force, placed on the operating stage 23, and a sample stage 25 on which to place the sample to be measured. On the sample stage 25 there are disposed a sample 26 to be measured, two circular columnar compression parts 27 in place of legs of the wearer, situated sandwiching the sample 26, and a stopper 28 for anchoring of one compression part.

The stand 22 (and operating stage 23) may be, for example, a digital force gauge stand, such as FGS-50X-H by Nidec-Shinpo Corp. The digital force gauge 24 may be a digital force gauge by Nidec-Shinpo Corp., such as FGP-0.5, mounting a press adapter (square, single side length: 15 mm). The compression part 27 may be, for example, a plastic plate by AS-one (weight: 38.5 g, diameter: 100 mm, height: 30 mm).

The sample 26, and specifically the cushion section removed out from the absorbent article, is placed between the two compression parts 27. The cushion section is set so that the two compression parts 27 compress the center location in the lengthwise direction of the cushion section in the widthwise direction of the cushion section. The lengthwise direction and widthwise direction of the cushion section are the lengthwise direction and widthwise direction of the absorbent article formed by the cushion section. The digital force gauge 24 is placed so that the adapter compresses in a manner centered around a location 6 mm below the compression part 27.

Next, the digital force gauge 24 is moved 20 mm so as to push down the sample 26 at a speed of 100 mm/min, compressing the sample 26, and the maximum value at that time is read off and used as the value for the compressive force.

In the absorbent article according to another embodiment of the present disclosure, the density of the cushion section forming the domed section differs between the outer peripheral section of the domed section and the center section, the density of the cushion section at the outer peripheral section being higher than the density of the cushion section at the center section (hereunder, the absorbent article will sometimes be referred to as "absorbent article including a cushion section with a density difference").

The shape of the labia minora of an adult female is not constant, but differs between individuals, and the labia minora of an adult female is more resistant to deformation when the body moves, compared to the labia majora. Also, deformation of the labia majora during body movement varies greatly depending on the body type of the woman, the labia majora tending to deform much more easily during body movement in slightly overweight women.

In an absorbent article including a cushion section with a density difference, the cushion section that has relatively low density at the center section of the domed section has low rigidity, and when it contacts with the labia minora, it deforms along the shape of the labia minora allowing it to embed the labia minora. However, the cushion section that has relatively high density at the outer peripheral section of the domed section has high rigidity, and it can continue to contact with the border between the labia minora and the labia majora, or with the labia majora, during periods of dryness before absorption of menstrual blood. Also, the cushion section that has relatively high density at the outer peripheral section of the domed section has high recoverability after compression, and therefore it can continue to contact with the complex-shaped excretory opening even during periods of wetness after menstrual blood has been absorbed.

As used herein, "excretory opening contact region" refers to the region bordering the excretory opening of the wearer, and "excretory opening" refers primarily to the labia minora, though not precluding that the outer peripheral section of the domed section borders with the labia majora.

Also, in an absorbent article including a cushion section with a density difference, since the center section of the domed section is easily compressed, it deforms with depressions along the shape of the labia minora of the wearer during use, embedding the labia minora, so that the top sheet closely contacts with the vaginal opening, and excessive spread of menstrual blood on the top sheet is prevented.

Also, since the top sheet closely contacts with the vaginal opening in an absorbent article including a cushion section with a density difference, the distance between the vaginal opening and the absorbent body is minimal during use, and when the cushion section is composed mainly of thermoplastic chemical fiber, menstrual blood passes through the top sheet and cushion section without diffusing in the planar directions during initial absorption of menstrual blood, and rapidly migrates into the absorbent body. Once a passage is formed for menstrual blood, the region becomes hydrophilicized, and therefore during a second or later absorption of menstrual blood, the menstrual blood still passes through the top sheet and cushion section and rapidly migrates into the absorbent body.

Furthermore, in an absorbent article including a cushion section with a density difference, even in cases where body pressure is applied and the bulk of the cushion section is temporarily reduced, such that a large amount of menstrual blood pools in the cushion section with the reduced bulk, the bulk of the cushion section rapidly recovers when the body pressure is weakened, starting with the outer peripheral section of the domed section, and menstrual blood thus rapidly migrates into the absorbent body.

The absorbent article including a cushion section with a density difference can be formed, for example, by embossing at least the top sheet and absorbent body near the outer edge of the cushion section.

By embossing at least the top sheet and the absorbent body in such a manner that the outer edge of the cushion section is compressed by tensile force of the embossed top sheet and absorbent body, creating a reduced thickness there, it is possible to increase the density of the cushion section at the outer peripheral section of the domed section above the density of the cushion section at the center section of the domed section. Also, since the degree of compression of the cushion section is low at the center section of the domed section and the thickness is not reduced as much as the outer peripheral section, the density of the cushion section does not easily increase.

An absorbent article including a cushion section with a density difference, and more specifically, an absorbent article having embossed sections formed by embossing at least the top sheet and the absorbent body near the outer edge of the cushion section, can be produced by (i) forming embossed sections by embossing the top sheet and absorbent body on the outside of the cushion section, or (ii) forming embossed sections by embossing the top sheet, cushion section and absorbent body on the outer edge of the cushion section.

Also, the absorbent article including a cushion section with a density difference can be produced by, for example, (i) embossing the outer edge of the cushion section, and then layering the liquid-impermeable back sheet, absorbent body, cushion section and top sheet in that order, (ii) layering the cushion section on the absorbent body, embossing the outer edge of the cushion section and the absorbent body together, and then layering the liquid-impermeable back sheet, embossed members and liquid-permeable top sheet in that order, or (iii) layering the cushion section on the liquid-permeable top sheet, embossing the outer edge of the cushion section and the top sheet together, and then layering the liquid-impermeable back sheet, absorbent body and embossed members in that order.

With compressed sections formed by compressing at least the top sheet and absorbent body near the outer edge of the cushion section, it is possible during periods of wetness after menstrual blood has been absorbed, for example, to minimize detachment of the top sheet from the absorbent body and to maintain the height of the density of the cushion section at the outer peripheral section of the domed section.

As used herein, the phrase "near the outer edge", as it relates to the cushion section, is a concept including not only the outer edge of the cushion section, but also an area inside the outer edge of the cushion section and an area outside the outer edge of the cushion section. Also, "near" means a range of preferably ±15%, more preferably ±10% and even more preferably ±5%, of the distance from the center of the cushion section to the outer edge of the cushion section, in the planar direction of the absorbent article.

The "center" of the cushion section is the center in the lengthwise direction and the widthwise direction of the absorbent article.

The embodiments shown in FIGS. 1 to 5 each have compressed sections formed by continuously compressing the top sheet and absorbent body on the outside of the cushion section, but in an absorbent article according to a different embodiment of the present disclosure, compressed sections are present that are formed by intermittently compressing the top sheet and absorbent body on the outside of the cushion section.

In an absorbent article according to yet another embodiment of the disclosure, compressed sections are present that are formed by continuously or intermittently compressing the top sheet, the cushion section and the absorbent body at the edge of the cushion section, and in an absorbent article according to yet another embodiment of the disclosure, compressed sections are present that are formed by continuously or intermittently compressing only the cushion section at the edge of the cushion section.

The embossed sections may be formed by a method known in the art, and for example, the embossed sections can be formed by using an upper and lower pair of embossing rolls, having a emboss pattern formed on one of the rolls, for embossing at a pressure of about 100 to about 1000 N/cm, at a temperature below the melting point of the fibers.

The shape of the cushion section before it is incorporated into the absorbent article is not particularly restricted, and for example, the projected form in the thickness direction of the absorbent article may have a shape similar to the labia minora, such as roughly circular, roughly elliptical, roughly rounded rectangular, or a figure surrounded by two arcs.

The cushion section may also have a constant thickness in the thickness direction of the absorbent article, or it may have a thickness that increases toward the outer edges from the center, or it may have a thickness that decreases toward the outer edges form the center.

When the thickness of the cushion section decreases from the center toward the outer edges, in cases where the absorbent body and top sheet have been embossed, it will often be difficult for the density of the cushion section at the outer peripheral section of the domed section to be increased above the density of the cushion section at the center section of the domed section, and therefore for the absorbent article including a cushion section with a density difference, it is preferred for the cushion section to have a constant thickness, or for the thickness to increase from the center toward the outer edges.

The cushion section may also have a different basis weight at different locations.

Figure 7:
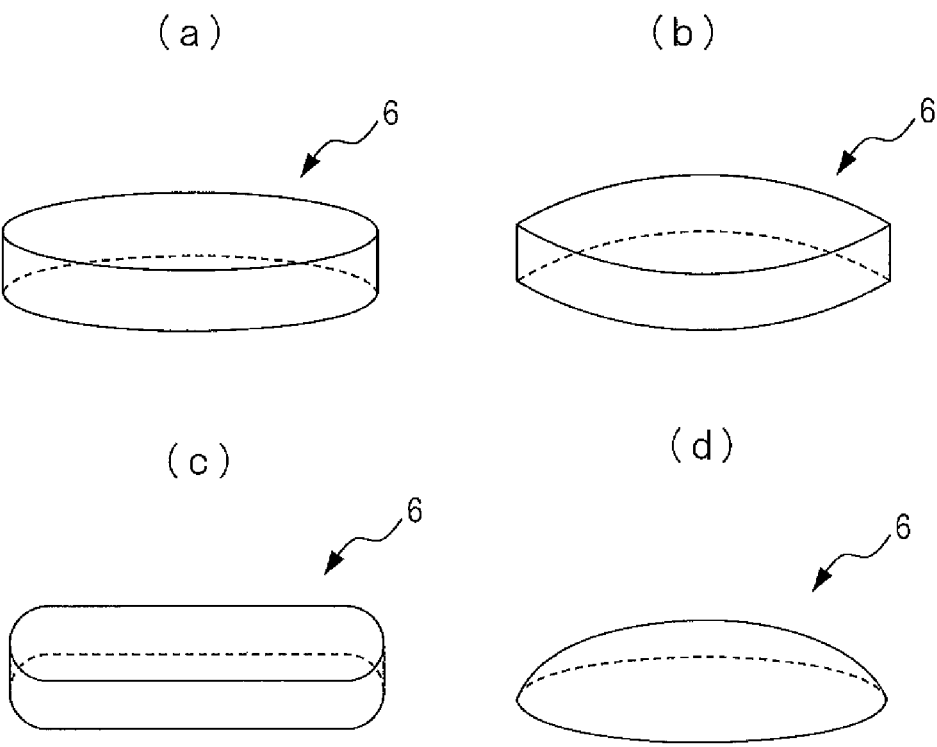
FIG. 7 is a diagram showing an example of the shape of a cushion section before it is incorporated into an absorbent article.

FIG. 7 is a diagram showing an example of the shape of a cushion section before it is incorporated into an absorbent article. The cushion section 6 shown in FIG. 7(a) is roughly elliptical in a projection drawing in the thickness direction of the absorbent article, and it has a constant thickness. The cushion section 6 shown in FIG. 7(b) has a shape consisting of two arcs in a projection drawing in the thickness direction of the absorbent article, and it has a constant thickness. The cushion section 6 shown in FIG. 7(c) is roughly rounded rectangular in a projection drawing in the thickness direction of the absorbent article, and it has a constant thickness. The cushion section 6 shown in FIG. 7(d) is roughly elliptical in a projection drawing in the thickness direction of the absorbent article, and it has a thickness that decreases from the center toward the outer edges.

The density of the cushion section at the center section of the domed section is preferably about 0.001 to 0.1 g/cm³, more preferably about 0.005 to about 0.08 g/cm³, and even more preferably about 0.01 to about 0.05 g/cm³. If the density is less than about 0.001 g/cm³, the compression recoverability will tend to be insufficient during wet periods after menstrual blood has been absorbed. If the density is greater than about 0.1 g/cm³, it will tend to deform along the labia minora of the wearer, resulting in more difficult fitting to the labia minora.

The density of the cushion section at the center section and outer peripheral section of the domed section is measured in the following manner.

(1) A two-dimensional laser displacement gauge is used to measure the thickness t (cm) of the cushion section at the measuring location. An example of such a two-dimensional laser displacement gauge is the LJ-G Series high precision two-dimensional laser displacement gauge (Model: LJ-G030) by Keyence Corp. The thickness of the cushion section at the measuring location is calculated by subtracting the thickness of the absorbent article in the region other than the cushion section from the thickness of the absorbent article at the measuring location.

(2) The cushion section is removed from the absorbent article and its basis weight b (g/m²) is measured. When the basis weight of the cushion section differs depending on the location, an approximately 15 mm×15 mm sample is taken centered on the measuring location, and its basis weight b (g/m²) is measured.

(3) The density d (g/cm³) is calculated by the following formula:

$$d=b/(10{,}000 \times t).$$

As indicated by this formula, if the basis weight of the cushion section is constant, the ratio of the density at locations other than the cushion section can be compared by the thickness alone. That is, when the basis weight of the cushion section is constant, a lower thickness of the cushion section represents a higher density of the cushion section.

In the absorbent article including a cushion section with a density difference, the density of the cushion section at the outer peripheral section of the domed section is higher than the density of the cushion section at the center section of the domed section, and preferably it is about 1.1 to about 5.0 times higher, more preferably about 1.2 to about 4.0 times higher and even more preferably about 1.5 to about 3.0 times higher. If the proportion is less than about 1.1 times higher, the compression recoverability of the cushion section at the outer peripheral section of the domed section will tend to be inadequate during periods of wetness, and if the proportion is greater than about 5.0 times higher, the rigidity of the cushion section at the outer peripheral section of the domed section will be increased, tending to leave the wearer with a feeling of the presence of a foreign object.

The cushion section has a length of preferably about 30 to about 200 mm, more preferably about 40 to about 170 mm and even more preferably about 50 to about 100 mm in the lengthwise direction of the absorbent article, and a length of preferably about 10 to about 100 mm, more preferably about 20 to about 70 mm and even more preferably about 25 to about 50 mm in the widthwise direction of the absorbent article.

If the size of the cushion section is within this range, the domed section will fit the excretory opening of the wearer, and especially the labia minora, during wearing, thus allowing leakage to be minimized. If the size of the cushion section is smaller than this range, the domed section will fail to fit the excretory opening of the wearer, and especially the labia minora, tending to result in leakage, while if the size of the cushion section is larger than this range, an uncomfortable feeling will tend to be noticed during wearing, or a gap will tend to form between the labia minora, resulting in easier leakage.

As used herein, unless otherwise specified, the term "lengthwise direction" means the lengthwise direction of the absorbent article, and the term "widthwise direction" means the widthwise direction of the absorbent article, while the "direction of thickness" means the thickness direction of the absorbent article.

The cushion section preferably retains at least about 50% of its maximum thickness, more preferably it retains at least about 60% of its maximum thickness and even more preferably it retains at least about 70% of its maximum thickness, after absorption of 2 g of horse EDTA blood, compared to before horse EDTA blood absorption. If this range of the maximum thickness is retained, the domed section including the cushion section will be resistant to collapse even during periods of wetness after menstrual blood has been absorbed, and the domed section will fit the excretory opening of the wearer, and especially the labia minora, thus reducing leakage.

The reason for dropping 2 g of horse EDTA blood is that the amount of menstrual blood excreted at once by a human is considered to be approximately 2 g. In order to absorb the horse EDTA blood into the cushion section, 2 g of horse EDTA blood is dropped onto the entire cushion section using a pipette, but when the cushion section comprises a water-repellent material, so that the horse EDTA blood is poorly taken up into the cushion section, the horse EDTA blood may be absorbed into the cushion section by applying pressure to the cushion section.

The maximum thickness of the cushion section after absorption of 2 g of horse EDTA blood is measured at 1 minute after all of the horse EDTA blood has been absorbed. The maximum thickness of the cushion section is also measured using the aforementioned two-dimensional laser displacement gauge.

The EDTA blood is described below.

In an absorbent article according to one embodiment of the present disclosure, as shown in FIG. 1, the absorbent article has a curved structure in which the domed section curves inward. If the absorbent article has a curved structure, the absorbent article will fit by curving with the body of the wearer, thus further helping to limit leakage of absorbed menstrual blood. The curved structure may be formed, for example, by passing an elastic member, such as rubber thread, expanding film or the like through both sides in the lengthwise direction of the absorbent article, and applying tensile force to both sides in the lengthwise direction of the absorbent article. In an absorbent article according to another embodiment of the present disclosure, the absorbent article has a flat structure in which the domed section does not curve inward.

In absorbent articles according to some embodiment of the present disclosure, the liquid-permeable top sheet has a plurality of ridges and a plurality of furrows on the skin contact surface, extending in the lengthwise direction of the absorbent article (throughout the present specification, the top sheet with a plurality of ridges and a plurality of furrows extending in the lengthwise direction of the absorbent article will sometimes be referred to simply as "top sheet with a ridge-furrow structure"). The top sheet can be produced by the method described in Japanese Unexamined Patent Publication No. 2008-025078, Japanese Unexamined Patent Publication No. 2008-025079, or elsewhere.

In an absorbent article according to certain embodiments of the present disclosure, the top sheet is a top sheet with a ridge-furrow structure, produced by the method described in Japanese Unexamined Patent Publication No. 2011-226010, Japanese Unexamined Patent Publication No. 2011-226011, or elsewhere. The top sheet with a ridge-furrow structure can be formed by passing the top sheet to be treated through the gap between a pair of gear rolls with rotational axis lines that are perpendicular to the machine direction, and rotating while a plurality of teeth situated on the peripheral surfaces of each of the gear rolls are mutually engaged, and subjecting it to fluid treatment.

Specifically, the draw ratio of the gear rolls is preferably about 105% or greater, more preferably about 105& to about 500%, even more preferably about 120% to 300%, and even more preferably about 130% to about 200%.

If the draw ratio is less than about 105%, the stretchability of the top sheet may be inadequate and the cushion section will more easily collapse during production of the absorbent article, while if the draw ratio is greater than about 500%, the top sheet will tend to tear during production of the absorbent article.

The term "draw ratio" refers to the value calculated by the following formula:

$$\text{Draw ratio (\%)} = 100 \times \left[ \frac{\sqrt{P^2 + 4D^2}}{P} - 1 \right]$$

where P is the gear pitch and D is the gear tooth cutting depth.

In absorbent articles according to some embodiment of the present disclosure, the liquid-permeable top sheet has a plurality of slits. If the liquid-permeable top sheet has a plurality of slits running through the top sheet, it will be possible to prevent widening of the slits and excessive collapse of the cushion section during production of the absorbent article. The top sheet with a plurality of slits can be formed by passing the top sheet through a slit roll having longitudinal slits arranged in a zigzag pattern.

The top sheet with a plurality of slits can be produced as described in Japanese Patent Public Inspection No. 2002-528174, for example.

In an absorbent article according to another embodiment of the disclosure, the liquid-permeable top sheet has a plurality of open pin holes.

A top sheet having a ridge-furrow structure, slits and open pin holes can prevent excessive collapse of the cushion section during production of the absorbent article, due to change of the shape of the ridge-furrow structure of the top sheet, and opening and closing of the slits and open pin holes. From this viewpoint, the ridge-furrow structure, slits and open pin holes of the top sheet are preferably present at least at the section bordering the cushion section, i.e. the section composing the domed section, but they may also be present over the entire top sheet.

In the absorbent article of the present disclosure, the shape of the absorbent body is not particularly restricted so long as it is a shape suited to the female body and the shape of shorts, such as rectangular, elliptical or gourd-shaped.

In the absorbent article of the present disclosure, the center section of the domed section can continue to embed the labia minora of the wearer, and its bulk will promptly recover even when the domed section is temporarily collapsed (such as when body pressure is applied by the wearer or menstrual blood is excreted), the center section of the domed section embedding the labia minora of the wearer and allowing continuous contact of the center section of the domed section with the labia minora. The absorbent body in the absorbent article of the present disclosure can therefore be reduced in size compared to the prior art.

In the absorbent article of the present disclosure, the absorbent body has a length of preferably about 80 to about 230 mm, more preferably about 100 to 200 mm and even more preferably about 120 to 170 mm in the lengthwise direction. Also, in the absorbent article of the present disclosure, the absorbent body has a length of preferably about 30 to about 90 mm, more preferably about 35 to 80 mm and even more preferably about 40 to 70 mm in the widthwise direction.

If the length in the lengthwise direction exceeds about 230 mm, or the length in the widthwise direction exceeds about 90 mm, the absorbent body will contact the gluteal region, groin and inner thighs of the wearer, creating a feeling of discomfort for the wearer, and potentially causing skin troubles for wearers with sensitive skin. Also, if the length in the lengthwise direction exceeds about 230 mm or the length in the widthwise direction exceeds about 90 mm, shifting of the absorbent body will tend to occur, resulting in formation of a gap between the absorbent article and the skin, and often causing leakage.

On the other hand, if the length in the lengthwise direction is less than about 80 mm or the length in the widthwise direction is less than about 30 mm, the absorption volume of the absorbent body will tend to be insufficient, and a feeling of psychological anxiety may be created before wear.

Also, if the highly-rigid absorbent body has an excessive size in the absorbent article, the domed section will not be able to easily contact the excretory opening, and especially the labia minora.

The absorbent article of the present disclosure may have any desired shape, such as a rectangular, elliptical or gourd-shape, and it may also have a flap to prevent slipping of clothing, such as shorts.

The absorbent article of the present disclosure can be reduced in size because it is resistant to leakage, allowing the absorbent body to be reduced in size.

The absorbent article of the present disclosure has a length in the lengthwise direction of preferably about 100 to about 260 mm, more preferably about 120 to about 220 mm and even more preferably about 150 to about 190 mm, and a length in the widthwise direction (without the flap sections) of preferably about 40 to about 100 mm, more preferably about 45 to about 90 mm and even more preferably about 50 to 80 mm.

In an absorbent article according to another embodiment of the present disclosure, the domed section comprises a blood modifying agent having an IOB of about 0.00-0.60, a melting point of about 45° C. or less, and a water solubility of about 0.00-0.05 g in 100 g of water at 25° C.

The IOB (Inorganic Organic Balance) is an indicator of the hydrophilic-lipophilic balance, and as used herein, it is the value calculated by the following formula by Oda et al.:

IOB=inorganic value/organic value.

The inorganic value and the organic value are based on the organic paradigm described in "Organic compound predictions and organic paradigms" by Fujita A., Kagaku no Ryoiki (Journal of Japanese Chemistry), Vol. 11, No. 10 (1957) p. 719-725.

The organic values and inorganic values of major groups, according to Fujita, are summarized in Table 1 below.

TABLE 1

| Group | Inorganic value | Organic value |
| --- | --- | --- |
| —COOH | 150 | 0 |
| —OH | 100 | 0 |
| —O—CO—O— | 80 | 0 |
| —CO— | 65 | 0 |
| —COOR | 60 | 0 |
| —O— | 20 | 0 |
| Triple bond | 3 | 0 |
| Double bond | 2 | 0 |
| $CH_2$ | 0 | 20 |
| iso-branch | 0 | −10 |
| tert-branch | 0 | −20 |
| Light metal (salt) | ≥500 | 0 |
| Heavy metal (salt), amine, $NH_3$ salt | ≥400 | 0 |

For example, in the case of an ester of tetradecanoic acid which has 14 carbon atoms and dodecyl alcohol which has 12 carbon atoms, the organic value is 520 ($CH_2$, 20×26) and the inorganic value is 60 (—COOR, 60×1), and therefore IOB=0.12.

In the blood modifying agent, the IOB is about 0.00-0.60, preferably about 0.00-0.50, more preferably about 0.00-0.40 and even more preferably about 0.00-0.30. This is because a lower IOB is associated with higher organicity and higher affinity with blood cells.

As used herein, the term "melting point" refers to the peak top temperature for the endothermic peak during conversion from solid to liquid, upon measurement with a differential scanning calorimetry analyzer at a temperature-elevating rate of 10° C./min. The melting point may be measured using a Model DSC-60 DSC measuring apparatus by Shimadzu Corp., for example.

If the blood modifying agent has a melting point of about 45° C. or less, it may be either liquid or solid at room temperature, or in other words, the melting point may be either about 25° C. or higher or below about 25° C., and for example, it may have a melting point of about −5° C. or about −20° C. The reason for a melting point of about 45° C. or less for the blood modifying agent will be explained below.

The blood modifying agent does not have a lower limit for the melting point, but the vapor pressure is preferably low. The vapor pressure of the blood modifying agent is preferably about 0-200 Pa, more preferably about 0-100 Pa, even more preferably about 0-10 Pa, even more preferably about 0-1 Pa, and even more preferably about 0.0-0.1 Pa at 25° C. (1 atmosphere).

Considering that the absorbent article of this disclosure is to be used in contact with the human body, the vapor pressure is preferably about 0-700 Pa, more preferably about 0-100 Pa, even more preferably about 0-10 Pa, even more preferably about 0-1 Pa, and even more preferably 0.0-0.1 Pa, at 40° C. (1 atmosphere). If the vapor pressure is high, gasification may occur during storage and the amount of blood modifying agent may be reduced, and as a consequence problems, such as odor during wear, may be created.

The melting point of the blood modifying agent may also differ depending on the weather or duration of wear. For example, in regions with a mean atmospheric temperature of about 10° C. or less, using a blood modifying agent with a melting point of about 10° C. or less allows the blood modifying agent to stably modify blood after excretion of menstrual blood, even if it has been cooled by the ambient temperature.

Also, when the absorbent article is used for a prolonged period of time, the melting point of the blood modifying agent is preferably at the high end of the range of about 45° C. or less. This is because the blood modifying agent is not easily affected by sweat or friction during wearing, and will not easily migrate even during prolonged wearing.

A water solubility of 0.00-0.05 g can be confirmed by adding 0.05 g of sample to 100 g of deionized water at 25° C., allowing the mixture to stand for 24 hours, and gently stirring after 24 hours if necessary and then visually evaluating whether or not the sample has dissolved.

The term "solubility" used herein in regard to water solubility includes cases where the sample completely dissolves in deionized water to form a homogeneous mixture, and cases where the sample is completely emulsified. Here, "completely" means that no mass of the sample remains in the deionized water.

In the art, top sheet surfaces are coated with surfactants in order to alter the surface tension of blood and promote rapid absorption of blood. However, because surfactants generally have high water solubility, the surfactant-coated top sheet is highly miscible with hydrophilic components (such as, blood plasma) in the blood and therefore, instead, they tend to cause residue of blood on the top sheet. The aforementioned blood modifying agent has low water solubility and therefore, unlike conventionally known surfactants, it does not cause residue of blood on the top sheet and allows rapid migration into the absorbent body.

As used herein, a water solubility in 100 g of water at 25° C. may be simply referred to as "water solubility".

As used herein, "weight-average molecular weight" includes the concept of a polydisperse compound (for example, a compound produced by stepwise polymerization, an ester formed from a plurality of fatty acids and a plurality of aliphatic monohydric alcohols), and a simple compound (for example, an ester formed from one fatty acid and one aliphatic monohydric alcohol), and in a system comprising $N_i$ molecules with molecular weight $M_i$ (i=1, or i=1, 2 . . .), it refers to $M_w$ determined by the following formula.

$$M_w = \Sigma N_i M_i^2 / \Sigma N_i M_i$$

As used herein, the weight-average molecular weights are the values measured by gel permeation chromatography (GPC), based on polystyrene.

The GPC measuring conditions may be the following, for example.

Device: Lachrom Elite high-speed liquid chromatogram by Hitachi High-Technologies Corp.

Columns: SHODEX KF-801, KF-803 and KF-804, by Showa Denko K.K.

Eluent: THF

Flow rate: 1.0 mL/min

Driving volume: 100 μL

Detection: RI (differential refractometer)

The weight-average molecular weights listed in the examples of the present specification were measured under the conditions described below.

Preferably, the blood modifying agent is selected from the group consisting of following items (i)-(iii), and any combination thereof:

(i) a hydrocarbon;

(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting for a hydrogen of the hydrocarbon moiety.

As used herein, "hydrocarbon" refers to a compound composed of carbon and hydrogen, and it may be a chain hydrocarbon, such as a paraffinic hydrocarbon (containing no double bond or triple bond, also referred to as alkane), an olefin-based hydrocarbon (containing one double bond, also referred to as alkene), an acetylene-based hydrocarbon (containing one triple bond, also referred to as alkyne), or a hydrocarbon comprising two or more bonds selected from the group consisting of double bonds and triple bonds, and cyclic hydrocarbon, such as aromatic hydrocarbons and alicyclic hydrocarbons.

Preferred as such hydrocarbons are chain hydrocarbons and alicyclic hydrocarbons, with chain hydrocarbons being more preferred, paraffinic hydrocarbons, olefin-based hydrocarbons and hydrocarbons with two or more double bonds (containing no triple bond) being more preferred, and paraffinic hydrocarbons being even more preferred.

Chain hydrocarbons include linear hydrocarbons and branched hydrocarbons.

When two or more oxy groups (—O—) are inserted in the compounds of (ii) and (iii) above, the oxy groups (—O—) are not adjacent each other. Thus, compounds (ii) and (iii) do not include compounds with continuous oxy groups (i.e., peroxides).

In the compounds of (iii), compounds in which at least one hydrogen on the hydrocarbon moiety is substituted with a hydroxyl group (—OH) are preferred over compounds in which at least one hydrogen on the hydrocarbon moiety is substituted with a carboxyl group (—COOH). As shown in Table 1, the carboxyl groups bond with metals and the like in menstrual blood, drastically increasing the inorganic value from 150 to 400 or greater, and therefore a blood modifying agent with carboxyl groups can increase the IOB value to more than about 0.60 during use, potentially lowering the affinity with blood cells.

More preferably, the blood modifying agent is selected from the group consisting of following items (i')-(iii'), and any combination thereof:

(i') a hydrocarbon;

(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting for a hydrogen on the hydrocarbon moiety.

When 2 or more same or different bonds are inserted in the compound of (ii') or (iii'), i.e., when 2 or more same or different bonds selected from the group consisting carbonyl bonds (—CO—), ester bonds (—COO—), carbonate bonds (—OCOO—) and ether bonds (—O—) are inserted, the bonds are not adjacent to each other, and at least one carbon atom lies between each of the bonds.

The blood modifying agent is more preferably a compound with no more than about 1.8 carbonyl bonds (—CO—), no more than 2 ester bonds (—COO—), no more than about 1.5 carbonate bonds (—OCOO—), no more than about 6 ether bonds (—O—), no more than about 0.8 carboxyl groups (—COOH) and/or no more than about 1.2 hydroxyl groups (—OH), per 10 carbon atoms in the hydrocarbon moiety.

Even more preferably, the blood modifying agent is selected from the group consisting of following items (A)-(F), and any combination thereof:

(A) an ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety;

(B) an ether of (B1) a compound having a chain hydrocarbon moiety and 2-4 hydroxyl groups substituting for hydrogens on the chain hydrocarbon moiety, and (B2) a compound having a chain hydrocarbon moiety and 1 hydroxyl group substituting for a hydrogen on the chain hydrocarbon moiety;

(C) an ester of (C1) a carboxylic acid, hydroxy acid, alkoxy acid or oxoacid comprising a chain hydrocarbon moiety and 2-4 carboxyl groups substituting for hydrogens on the chain hydrocarbon moiety, and (C2) a compound having a chain hydrocarbon moiety and 1 hydroxyl group substituting for a hydrogen on the chain hydrocarbon moiety;

(D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;

(E) a polyoxy $C_2$-$C_6$ alkylene glycol, or ester or ether thereof; and (F) a chain hydrocarbon.

The blood modifying agent in accordance with (A) to (F) will now be described in detail.

[(A) Ester of (A1) a Compound Having a Chain Hydrocarbon Moiety and 2-4 Hydroxyl Groups Substituting for Hydrogens on the Chain Hydrocarbon Moiety, and (A2) a Compound Having a Chain Hydrocarbon Moiety and 1 Carboxyl Group Substituting for a Hydrogen on the Chain Hydrocarbon Moiety]

In the (A) ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety (hereunder also referred to as "compound (A)"), it is not necessary for all of the hydroxyl groups to be esterified so long as the IOB, melting point and water solubility are within the aforementioned ranges.

Examples of (A1) a compound having a chain hydrocarbon moiety and 2-4 hydroxyl groups substituting for hydrogens on the chain hydrocarbon moiety (hereunder also referred to as "compound (A1)") include chain hydrocarbon tetraols, such as alkanetetraols, including pentaerythritol, chain hydrocarbon triols, such as alkanetriols, including glycerins, and chain hydrocarbon diols, such as alkanediols, including glycols.

Examples of (A2) a compound having a chain hydrocarbon moiety and 1 carboxyl group substituting for a hydrogen on the chain hydrocarbon moiety (hereunder also referred to as "compound (A2)") include compounds in which one hydrogen on the hydrocarbon is substituted with one carboxyl group (—COOH), such as fatty acids.

Examples for compound (A) include ($a_1$) an ester of a chain hydrocarbon tetraol and at least one fatty acid, ($a_2$) an ester of a chain hydrocarbon triol and at least one fatty acid, and (a₃) an ester of a chain hydrocarbon diol and at least one fatty acids.

[(a₁) Esters of a Chain Hydrocarbon Tetraol and at Least One Fatty Acid]

Examples of an ester of a chain hydrocarbon tetraol and at least one fatty acid include tetraesters of pentaerythritol and fatty acids, represented by the following formula (1):

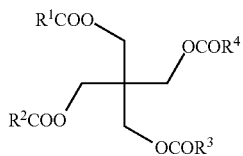

(1)

triesters of pentaerythritol and fatty acids, represented by the following formula (2):

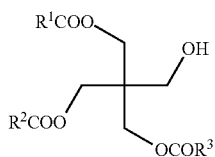

(2)

diesters of pentaerythritol and fatty acids, represented by the following formula (3):

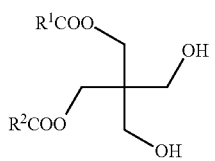

(3)

and monoesters of pentaerythritol and fatty acids, represented by the following formula (4).

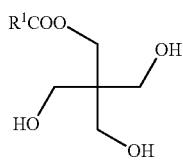

(4)

In the formulas, $R^1$-$R^4$ each represent a chain hydrocarbon.

The fatty acids consisting of the esters of pentaerythritol and fatty acids ($R^1$COOH, $R^2$COOH, $R^3$COOH, and $R^4$COOH) are not particularly restricted so long as the pentaerythritol and fatty acid esters satisfy the conditions for the IOB, melting point and water solubility, and for example, there may be mentioned saturated fatty acids, such as a $C_2$-$C_{30}$ saturated fatty acids, including acetic acid ($C_2$) ($C_2$ representing the number of carbons, corresponding to the number of carbons of each of $R^1C$, $R^2C$, $R^3C$ or $R^4C$, same hereunder), propanoic acid ($C_3$), butanoic acid ($C_4$) and its isomers, such as 2-methylpropanoic acid ($C_4$), pentanoic acid ($C_5$) and its isomers, such as 2-methylbutanoic acid ($C_5$) and 2,2-dimethylpropanoic acid ($C_5$), hexanoic acid ($C_6$), heptanoic acid ($C_7$), octanoic acid ($C_8$) and its isomers, such as 2-ethylhexanoic acid ($C_8$), nonanoic acid ($C_9$), decanoic acid ($C_{10}$), dodecanoic acid ($C_{12}$), tetradecanoic acid ($C_{14}$), hexadecanoic acid ($C_{16}$), heptadecanoic acid ($C_{17}$), octadecanoic acid ($C_{18}$), eicosanoic acid ($C_{20}$), docosanoic acid ($C_{22}$), tetracosanoic acid ($C_{24}$), hexacosanoic acid ($C_{26}$), octacosanoic acid ($C_{28}$), triacontanoic acid ($C_{30}$), as well as isomers of the foregoing (excluding those mentioned above).

The fatty acid may also be an unsaturated fatty acid. Examples of unsaturated fatty acids include $C_3$-$C_{20}$ unsaturated fatty acids, such as monounsaturated fatty acids including crotonic acid ($C_4$), myristoleic acid ($C_{14}$), palmitoleic acid ($C_{16}$), oleic acid ($C_{18}$), elaidic acid ($C_{18}$), vaccenic acid ($C_{18}$), gadoleic acid ($C_{20}$) and eicosenoic acid ($C_{20}$), di-unsaturated fatty acids including linolic acid ($C_{18}$) and eicosadienoic acid ($C_{20}$), tri-unsaturated fatty acids including linolenic acids, such as α-linolenic acid ($C_{18}$) and γ-linolenic acid ($C_{18}$), pinolenic acid ($C_{18}$), eleostearic acids, such as α-eleostearic acid ($C_{18}$) and β-eleostearic acid ($C_{18}$), Mead acid ($C_{20}$), dihomo-γ-linolenic acid ($C_{20}$) and eicosatrienoic acid ($C_{20}$), tetra-unsaturated fatty acids including stearidonic acid ($C_{20}$), arachidonic acid ($C_{20}$) and eicosatetraenoic acid ($C_{20}$), penta-unsaturated fatty acids including bosseopentaenoic acid ($C_{18}$) and eicosapentaenoic acid ($C_{20}$), and partial hydrogen adducts of the foregoing.

Considering the potential for degradation by oxidation and the like, the ester of pentaerythritol and a fatty acid is preferably an ester of pentaerythritol and a fatty acid, which is derived from a saturated fatty acid, i.e., an ester of pentaerythritol and a saturated fatty acid.

Also, in order to lower the IOB and result in greater hydrophobicity, the ester of pentaerythritol and a fatty acid is preferably a diester, triester or tetraester, more preferably a triester or tetraester, and even more preferably a tetraester.

In a tetraester of pentaerythritol and a fatty acid, the IOB is 0.60 if the total number of carbons of the fatty acid consisting of the tetraester of the pentaerythritol and fatty acid, i.e., the total number of carbons of the $R^1C$, $R^2C$, $R^3C$ and $R^4C$ portions in formula (1), is 15. Thus, when the total number of carbons of the fatty acid consisting of the tetraester of the pentaerythritol and fatty acid is approximately 15 or greater, the IOB satisfies the condition of being within about 0.00 to 0.60.

Examples of tetraesters of pentaerythritol and fatty acids include tetraesters of pentaerythritol with hexanoic acid ($C_6$), heptanoic acid ($C_7$), octanoic acid ($C_8$), such as 2-ethylhexanoic acid ($C_8$), nonanoic acid ($C_9$), decanoic acid ($C_{10}$) and/or dodecanoic acid ($C_{12}$).

In a triester of pentaerythritol and a fatty acid, the IOB is 0.58 if the total number of carbons of the fatty acid consisting of the triester of the pentaerythritol and fatty acid, i.e., the total number of carbons of the $R^1C$, $R^2C$ and $R^3C$ portions in formula (2), is 19. Thus, when the total number of carbons of the fatty acid consisting of the triester of the pentaerythritol and fatty acid is approximately 19 or greater, the IOB satisfies the condition of being within about 0.00 to 0.60.

In a diester of pentaerythritol and a fatty acid, the IOB is 0.59 if the total number of carbons of the fatty acid consisting of the diester of the pentaerythritol and fatty acid, i.e., the total number of carbons of the $R^1C$ and $R^2C$ portion in formula (3), is 22. Thus, when the total number of carbons of the fatty acid consisting of the diester of the pentaerythritol and fatty acid is approximately 22 or greater, the IOB satisfies the condition of being within about 0.00 to 0.60.

In a monoester of pentaerythritol and a fatty acid, the IOB is 0.60 if the total number of carbons of the fatty acid consisting of the monoester of the pentaerythritol and fatty acid, i.e. the total number of carbons of the $R^1C$ portion in formula (4), is 25. Thus, when the number of carbons of the fatty acid consisting of the monoester of the pentaerythritol and fatty acid is approximately 25 or greater, the IOB satisfies the condition of being within about 0.00 to 0.60.

The effects of double bonds, triple bonds, iso-branches and tert-branches are not considered in this calculation.

Commercial products which are esters of pentaerythritol and fatty acids include UNISTAR H-408BRS and H-2408BRS-22 (mixed product) (both products of NOF Corp.).

[($a_2$) Ester of a Chain Hydrocarbon Triol and at Least One Fatty Acid]

Examples of esters of a chain hydrocarbon triol and at least one fatty acid include triesters of glycerin and fatty acids, represented by formula (5):

diesters of glycerin and fatty acids, represented by the following formula (6):

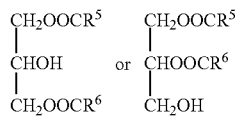

and monoesters of glycerin and fatty acids, represented by the following formula (7):

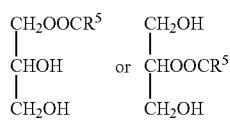

wherein $R^5$-$R^7$ each represent a chain hydrocarbon.

The fatty acid consisting of the ester of glycerin and a fatty acid ($R^5$COOH, $R^6$COOH and $R^7$COOH) is not particularly restricted so long as the ester of glycerin and a fatty acid satisfies the conditions for the IOB, melting point and water solubility, and for example, there may be mentioned the fatty acids mentioned for the "($a_1$) Ester of a chain hydrocarbon tetraol and at least one fatty acid", namely saturated fatty acids and unsaturated fatty acids, and in consideration of the potential for degradation by oxidation and the like, the ester is preferably a glycerin and fatty acid ester, which is derived from a saturated fatty acid, i.e., an ester of glycerin and a saturated fatty acid.

Also, in order to lower the IOB and result in greater hydrophobicity, the ester of glycerin and a fatty acid is preferably a diester or triester, and more preferably a triester.

A triester of glycerin and a fatty acid is also known as a triglyceride, and examples include triesters of glycerin and octanoic acid ($C_8$), triesters of glycerin and decanoic acid ($C_{10}$), triesters of glycerin and dodecanoic acid ($C_{12}$), triesters of glycerin and 2 or more different fatty acids, and mixtures of the foregoing.

Examples of triesters of glycerin and 2 or more fatty acids include triesters of glycerin with octanoic acid ($C_8$) and decanoic acid ($C_{10}$), triesters of glycerin with octanoic acid ($C_8$), decanoic acid ($C_{10}$) and dodecanoic acid ($C_{12}$), and triesters of glycerin with octanoic acid ($C_8$), decanoic acid ($C_n$), dodecanoic acid ($C_{12}$), tetradecanoic acid ($C_{14}$), hexadecanoic acid ($C_{16}$) and octadecanoic acid ($C_n$).

In order to obtain a melting point of about 45° C. or less, preferred triesters of glycerin and fatty acids are those with no more than about 40 as the total number of carbons of the fatty acid consisting of the triester of glycerin and the fatty acid, i.e., the total number of carbons of the $R^5C$, $R^6C$ and $R^7C$ sections in formula (5).

In a triester of glycerin and a fatty acid, the IOB value is 0.60 when the total number of carbons of the fatty acid consisting of the triester of glycerin and the fatty acid, i.e., the total number of carbons of the $R^5C$, $R^6C$ and $R^7C$ portions in formula (5), is 12. Thus, when the total number of carbons of the fatty acid consisting of the triester of the glycerin and fatty acid is approximately 12 or greater, the IOB satisfies the condition of being within about 0.00 to 0.60.

Triesters of glycerin and fatty acids, being aliphatic and therefore potential constituent components of the human body are preferred from the viewpoint of safety.

Commercial products of triesters of glycerin and fatty acids include tri-coconut fatty acid glycerides, NA36, PANACET 800, PANACET 800B and PANACET 810S, and tri-C2L oil fatty acid glycerides and tri-CL oil fatty acid glycerides (all products of NOF Corp.).

A diester of glycerin and a fatty acid is also known as a diglyceride, and examples include diesters of glycerin and decanoic acid ($C_{10}$), diesters of glycerin and dodecanoic acid ($C_{12}$), diesters of glycerin and hexadecanoic acid ($C_{16}$), diesters of glycerin and 2 or more different fatty acids, and mixtures of the foregoing.

In a diester of glycerin and a fatty acid, the IOB is 0.58 if the total number of carbons of the fatty acid consisting of the diester of the glycerin and fatty acid, i.e., the total number of carbons of the $R^5C$ and $R^6C$ portions in formula (6), is 16. Thus, when the total number of carbons of the fatty acid consisting of the diester of the glycerin and fatty acid is approximately 16 or greater, the IOB satisfies the condition of being about 0.00 to 0.60.

Monoesters of glycerin and fatty acids are also known as monoglycerides, and examples include glycerin and eicosanoic acid ($C_{20}$) monoester, and glycerin and docosanoic acid ($C_{22}$) monoester.

In a monoester of glycerin and a fatty acid, the IOB is 0.59 if the total number of carbons of the fatty acid consisting of the monoester of the glycerin and fatty acid, i.e. the number of carbons of the $R^5C$ portion in formula (7), is 19. Thus, when the number of carbons of the fatty acid consisting of the monoester of the glycerin and fatty acid is approximately 19 or greater, the IOB satisfies the condition of being about 0.00 to 0.60.

[($a_3$) Ester of a Chain Hydrocarbon Diol and at Least One Fatty Acid]

Examples of an ester of a chain hydrocarbon diol and at least one fatty acid include monoesters and diesters of fatty acids with $C_2$-$C_6$ chain hydrocarbon diols, such as $C_2$-$C_6$ glycols, including ethylene glycol, propylene glycol, butylene glycol, pentylene glycol and hexylene glycol.

Specifically, examples of an ester of a chain hydrocarbon diol and at least one fatty acid include diesters of $C_2$-$C_6$ glycols and fatty acids, represented by the following formula (8):

$$R^8COOC_kH_{2k}OCOR^9 \qquad (8)$$

wherein k represents an integer of 2-6, and $R^8$ and $R^9$ each represent a chain hydrocarbon, and monoesters of $C_2$-$C_6$ glycols and fatty acids, represented by the following formula (9):

$$R^8COOC_kH_{2k}OH \qquad (9)$$

wherein k represents an integer of 2-6, and $R^8$ is a chain hydrocarbon.

The fatty acid to be esterified in an ester of a $C_2$-$C_6$ glycol and a fatty acid (corresponding to $R^8COOH$ and $R^9COOH$ in formula (8) and formula (9)) is not particularly restricted so long as the ester of the $C_2$-$C_6$ glycol and fatty acid satisfies the conditions for the IOB, melting point and water solubility, and for example, there may be mentioned the fatty acids mentioned above for the "($a_1$) Ester of a chain hydrocarbon tetraol and at least one fatty acid", namely saturated fatty acids and unsaturated fatty acids, and in consideration of the potential for degradation by oxidation and the like, it is preferably a saturated fatty acid.

In a diester of butylene glycol (k=4) and a fatty acid represented by formula (8), IOB is 0.60 when the total number of carbons of the $R^8C$ and $R^9C$ portions is 6. Thus, when the total number of carbon atoms in a diester of butylene glycol (k=4) and a fatty acid represented by formula (8) is approximately 6 or greater, the IOB satisfies the condition of being about 0.00-0.60. In a monoester of ethylene glycol (k=2) and a fatty acid represented by formula (9), IOB is 0.57 when the total number of carbons of the $R^8C$ portion is 12. Thus, when the total number of carbon atoms in the fatty acid consisting of a monoester of ethylene glycol (k=2) and a fatty acid represented by formula (9) is approximately 12 or greater, the IOB satisfies the condition of being about 0.00-0.60.

Considering the potential for degradation by oxidation and the like, the ester of the $C_2$-$C_6$ glycol and fatty acid is preferably a $C_2$-$C_6$ glycol and fatty acid ester derived from a saturated fatty acid, or in other words, an ester of a $C_2$-$C_6$ glycol and a saturated fatty acid.

Also, in order to lower the IOB and result in greater hydrophobicity, the ester of the $C_2$-$C_6$ glycol and fatty acid is preferably a glycol and fatty acid ester derived from a glycol with a greater number of carbons, such as an ester of a glycol and a fatty acid derived from butylene glycol, pentylene glycol or hexylene glycol.

Also, in order to lower the IOB and result in greater hydrophobicity, the ester of a $C_2$-$C_6$ glycol and fatty acid is preferably a diester.

Examples of commercial products of esters of $C_2$-$C_6$ glycols and fatty acids include COMPOL BL and COMPOL BS (both products of NOF Corp.).

[(B) Ether of (B1) a Compound Having a Chain Hydrocarbon Moiety and 2-4 Hydroxyl Groups Substituting for Hydrogens on the Chain Hydrocarbon Moiety and (B2) a Compound Having a Chain Hydrocarbon Moiety and 1 Hydroxyl Group Substituting for a Hydrogen on the Chain Hydrocarbon Moiety]

In the (B) ether of (B1) a compound having a chain hydrocarbon moiety and 2-4 hydroxyl groups substituting for hydrogens on the chain hydrocarbon moiety and (B2) a compound having a chain hydrocarbon moiety and 1 hydroxyl group substituting for hydrogen on the chain hydrocarbon moiety (hereunder also referred to as "compound (B)"), it is not necessary for all of the hydroxyl groups to be etherified so long as the IOB, melting point and water solubility are within the aforementioned ranges.

Examples of (B1) a compound having a chain hydrocarbon moiety and 2-4 hydroxyl groups substituting for hydrogens on the chain hydrocarbon moiety (hereunder also referred to as "compound (B1)") include those mentioned for "compound (A)" as compound (A1), such as pentaerythritol, glycerin and glycol.

Examples of (B2) a compound having a chain hydrocarbon moiety and 1 hydroxyl group substituting for a hydrogen on the chain hydrocarbon moiety (hereunder also referred to as "compound (B2)") include compounds wherein 1 hydrogen on the hydrocarbon is substituted with 1 hydroxyl group (—OH), such as aliphatic monohydric alcohols, including saturated aliphatic monohydric alcohols and unsaturated aliphatic monohydric alcohols.

Examples of saturated aliphatic monohydric alcohols include $C_1$-$C_{20}$ saturated aliphatic monohydric alcohols, such as methyl alcohol ($C_1$) ($C_1$ representing the number of carbon atoms, same hereunder), ethyl alcohol ($C_2$), propyl alcohol ($C_3$) and its isomers, including isopropyl alcohol ($C_3$), butyl alcohol ($C_4$) and its isomers, including sec-butyl alcohol ($C_4$) and tert-butyl alcohol ($C_4$), pentyl alcohol ($C_5$), hexyl alcohol ($C_6$), heptyl alcohol ($C_7$), octyl alcohol ($C_8$) and its isomers, including 2-ethylhexyl alcohol ($C_9$), nonyl alcohol ($C_9$), decyl alcohol ($C_{10}$), dodecyl alcohol ($C_{12}$), tetradecyl alcohol ($C_{14}$), hexadecyl alcohol ($C_{16}$), heptadecyl alcohol ($C_{17}$), octadecyl alcohol ($C_{18}$) and eicosyl alcohol ($C_{20}$), as well as their isomers other than those mentioned.

Unsaturated aliphatic monohydric alcohols include those wherein 1 C—C single bond of a saturated aliphatic monohydric alcohol mentioned above is replaced with a C═C double bond, such as oleyl alcohol, and for example, such alcohols are commercially available by New Japan Chemical Co., Ltd. as the RIKACOL Series and UNJECOL Series.

Examples for compound (B) include ($b_1$) an ether of a chain hydrocarbon tetraol and at least one aliphatic monohydric alcohol, such as monoethers, diethers, triethers and tetraethers, preferably diethers, triethers and tetraethers, more preferably triethers and tetraethers and even more preferably tetraethers, ($b_2$) an ether of a chain hydrocarbon triol and at least one aliphatic monohydric alcohol, such as monoethers, diethers and triethers, preferably diethers and triethers and more preferably triethers, and ($b_3$) an ether of a chain hydrocarbon diol and at least one aliphatic monohydric alcohol, such as monoethers and diethers, and preferably diethers.

Examples of an ether of a chain hydrocarbon tetraol and at least one aliphatic monohydric alcohol include tetraethers, triethers, diethers and monoethers of pentaerythritol and aliphatic monohydric alcohols, represented by the following formulas (10)-(13):

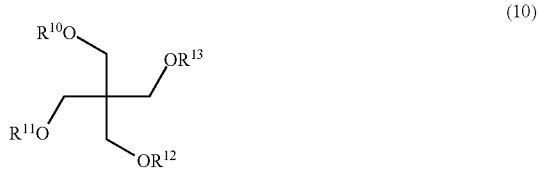

(10)

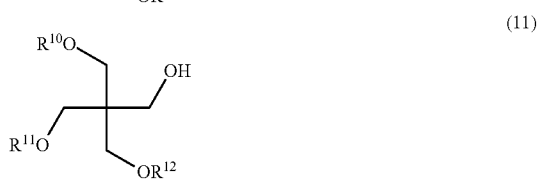

(11)

-continued

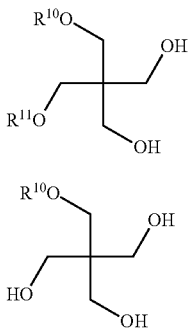
(12)

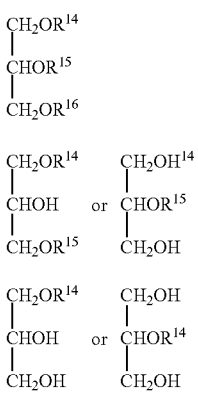
(13)

wherein $R^{10}$-$R^{13}$ each represent a chain hydrocarbon.

Examples of an ether of a chain hydrocarbon triol and at least one aliphatic monohydric alcohol include triethers, diethers and monoethers of glycerin and aliphatic monohydric alcohols, represented by the following formulas (14)-(16):

$$\begin{array}{l} CH_2OR^{14} \\ | \\ CHOR^{15} \\ | \\ CH_2OR^{16} \end{array} \quad (14)$$

$$\begin{array}{ll} CH_2OR^{14} & CH_2OH^{14} \\ | & | \\ CHOH \quad or \quad CHOR^{15} \\ | & | \\ CH_2OR^{15} & CH_2OH \end{array} \quad (15)$$

$$\begin{array}{ll} CH_2OR^{14} & CH_2OH \\ | & | \\ CHOH \quad or \quad CHOR^{14} \\ | & | \\ CH_2OH & CH_2OH \end{array} \quad (16)$$

wherein $R^{14}$-$R^{16}$ each represent a chain hydrocarbon.

Examples of an ether of a chain hydrocarbon diol and at least one aliphatic monohydric alcohol include diethers of $C_2$-$C_6$ glycols and aliphatic monohydric alcohols, represented by the following formula (17):

$$R^{17}OC_nH_{2n}OR^{18} \quad (17)$$

wherein n is an integer of 2-6, and $R^{17}$ and $R^{18}$ are each a chain hydrocarbon, and monoethers of $C_2$-$C_6$ glycols and aliphatic monohydric alcohols, represented by the following formula (18):

$$R^{17}OC_nH_{2n}OH \quad (18)$$

wherein n is an integer of 2-6, and $R^{17}$ is a chain hydrocarbon.

In the tetraether of pentaerythritol and an aliphatic monohydric alcohol, the IOB is 0.44 when the total number of carbon atoms of the aliphatic monohydric alcohol consisting of the tetraether of pentaerythritol and the aliphatic monohydric alcohol, i.e., the total number of carbon atoms of the $R^{10}$, $R^{11}$, $R^{12}$ and $R^{13}$ portions in formula (10), is 4. Thus, when the total number of carbon atoms of the aliphatic monohydric alcohol consisting of a tetraether of pentaerythritol and an aliphatic monohydric alcohol is approximately 4 or greater, the IOB value satisfies the condition of being within about 0.00 to 0.60.

In the triether of pentaerythritol and an aliphatic monohydric alcohol, the IOB is 0.57 when the total number of carbon atoms of the aliphatic monohydric alcohol consisting of the triether of pentaerythritol and the aliphatic monohydric alcohol, i.e., the total number of carbon atoms of the $R^{10}$, $R^{11}$ and $R^{12}$ portions in formula (11), is 9. Thus, when the total number of carbon atoms of the aliphatic monohydric alcohol consisting of a triether of pentaerythritol and an aliphatic monohydric alcohol is approximately 9 or greater, the IOB value satisfies the condition of being within about 0.00 to 0.60.

In the diether of pentaerythritol and an aliphatic monohydric alcohol, the IOB is 0.60 when the total number of carbon atoms of the aliphatic monohydric alcohol consisting of the diether of pentaerythritol and the aliphatic monohydric alcohol, i.e., the total number of carbon atoms of the $R^{10}$ and $R^{11}$ portions in formula (12), is 15. Thus, when the total number of carbon atoms of the aliphatic monohydric alcohol consisting of a diether of pentaerythritol and an aliphatic monohydric alcohol is approximately 15 or greater, the IOB value satisfies the condition of being within about 0.00 to 0.60.

In the monoether of pentaerythritol and an aliphatic monohydric alcohol, the IOB is 0.59 when the number of carbon atoms of the aliphatic monohydric alcohol consisting of the monoether of pentaerythritol and the aliphatic monohydric alcohol, i.e. the number of carbon atoms of the $R^{10}$ portion in formula (13), is 22. Thus, when the total number of carbon atoms of the aliphatic monohydric alcohol consisting of a monoether of pentaerythritol and an aliphatic monohydric alcohol is approximately 22 or greater, the IOB value satisfies the condition of being within about 0.00 to 0.60.

In the triether of glycerin and an aliphatic monohydric alcohol, the IOB is 0.50 when the total number of carbon atoms of the aliphatic monohydric alcohol consisting of the triether of glycerin and the aliphatic monohydric alcohol, i.e., the total number of carbon atoms of the $R^{14}$, $R^{15}$ and $R^{16}$ portions in formula (14), is 3. Thus, when the total number of carbon atoms of the aliphatic monohydric alcohol consisting of a triether of glycerin and an aliphatic monohydric alcohol is approximately 3 or greater, the IOB value satisfies the condition of being within about 0.00 to 0.60.

In the diether of glycerin and an aliphatic monohydric alcohol, the IOB is 0.58 when the total number of carbon atoms of the aliphatic monohydric alcohol consisting of the diether of glycerin and the aliphatic monohydric alcohol, i.e., the total number of carbon atoms of the $R^{14}$ and $R^{15}$ portions in formula (15), is 9. Thus, when the total number of carbon atoms of the aliphatic monohydric alcohol consisting of a diether of glycerin and an aliphatic monohydric alcohol is approximately 9 or greater, the IOB value satisfies the condition of being within about 0.00 to 0.60.

In the monoether of glycerin and an aliphatic monohydric alcohol, the IOB is 0.58 when the number of carbon atoms of the aliphatic monohydric alcohol consisting of the monoether of glycerin and the aliphatic monohydric alcohol, i.e., the number of carbon atoms of the $R^{14}$ portion in formula (16), is 16. Thus, when the total number of carbon atoms of the aliphatic monohydric alcohol consisting of a monoether of glycerin and an aliphatic monohydric alcohol is approximately 16 or greater, the IOB value satisfies the condition of being within about 0.00 to 0.60.

In a diether of butylene glycol (n=4) and aliphatic monohydric alcohol represented by formula (17), the IOB is 0.33 when the total number of carbon atoms of the $R^{17}$ and $R^{18}$ portions is 2. Thus, when the number of carbon atoms of the aliphatic monohydric alcohol in a diether of butylene glycol (n=4) and an aliphatic monohydric alcohol represented by formula (17) is approximately 2 or greater, the IOB value satisfies the condition of being within about 0.00-0.60. Also, in a monoether of ethylene glycol (n=2) and aliphatic monohydric alcohol represented by formula (18), the IOB is 0.60 when the number of carbon atoms of the $R^{17}$ portion is 8. Thus, when the number of carbon atoms of the aliphatic monohydric alcohol consisting of a monoether of ethylene glycol (n=2) and an aliphatic monohydric alcohol represented by formula (18) is approximately 8 or greater, the IOB value satisfies the condition of being within about 0.00 to 0.60.

Compound (B) may be produced by dehydrating condensation of compound (B1) and compound (B2) in the presence of an acid catalyst.

[(C) Ester of (C1) a Carboxylic Acid, Hydroxy Acid, Alkoxy Acid or Oxoacid Comprising a Chain Hydrocarbon Moiety and 2-4 Carboxyl Groups Substituting for Hydrogens on the Chain Hydrocarbon Moiety and (C2) a Compound Having a Chain Hydrocarbon Moiety and 1 Hydroxyl Group Substituting for a Hydrogen on the Chain Hydrocarbon Moiety]

In the (C) ester of (C1) a carboxylic acid, hydroxy acid, alkoxy acid or oxoacid comprising a chain hydrocarbon moiety and 2-4 carboxyl groups substituting for hydrogens on the chain hydrocarbon moiety and (C2) a compound having a chain hydrocarbon moiety and 1 hydroxyl group substituting for a hydrogen on the chain hydrocarbon moiety (hereunder also referred to as "compound (C)"), it is not necessary for all of the carboxyl groups to be esterified so long as the IOB, melting point and water solubility are within the aforementioned ranges.

Examples of (C1) a carboxylic acid, hydroxy acid, alkoxy acid or oxoacid comprising a chain hydrocarbon moiety and 2-4 carboxyl groups substituting for hydrogens on the chain hydrocarbon moiety (hereunder also referred to as "compound (C1)") include chain hydrocarbon carboxylic acids with 2-4 carboxyl groups, such as chain hydrocarbon dicarboxylic acids including alkanedicarboxylic acids, such as ethanedioic acid, propanedioic acid, butanedioic acid, pentanedioic acid, hexanedioic acid, heptanedioic acid, octanedioic acid, nonanedioic acid and decanedioic acid, chain hydrocarbon tricarboxylic acids, including alkanetricarboxylic acids, such as propanetrioic acid, butanetrioic acid, pentanetrioic acid, hexanetrioic acid, heptanetrioic acid, octanetrioic acid, nonanetrioic acid and decanetrioic acid, and chain hydrocarbon tetracarboxylic acids, including alkanetetracarboxylic acids, such as butanetetraoic acid, pentanetetraoic acid, hexanetetraoic acid, heptanetetraoic acid, octanetetraoic acid, nonanetetraoic acid and decanetetraoic acid.

Compound (C1) includes chain hydrocarbon hydroxy acids with 2-4 carboxyl groups, such as malic acid, tartaric acid, citric acid and isocitric acid, chain hydrocarbon alkoxy acids with 2-4 carboxyl groups, such as O-acetylcitric acid, and chain hydrocarbon oxoacids with 2-4 carboxyl groups.

(C2) Compound having a chain hydrocarbon moiety and 1 hydroxyl group substituting for a hydrogen on the chain hydrocarbon moiety includes those mentioned for "compound (B)", such as aliphatic monohydric alcohols.

Compound (C) may be ($c_1$) an ester, for example a monoester, diester, triester or tetraester, preferably a diester, triester or tetraester, more preferably a triester or tetraester and even more preferably a tetraester, of a chain hydrocarbon tetracarboxylic acid, hydroxy acid, alkoxy acid or oxoacid with 4 carboxyl groups, and at least one aliphatic monohydric alcohol, ($c_2$) an ester, for example, a monoester, diester or triester, preferably a diester or triester and more preferably a triester, of a chain hydrocarbon tricarboxylic acid, hydroxy acid, alkoxy acid or oxoacid with 3 carboxyl groups, and at least one aliphatic monohydric alcohol, or ($c_3$) an ester, for example, a monoester or diester, and preferably a diester, of a chain hydrocarbon dicarboxylic acid, hydroxy acid, alkoxy acid or oxoacid with 2 carboxyl groups, and at least one aliphatic monohydric alcohol.

Examples for compound (C) include dioctyl adipate, diisostearyl malate, tributyl citrate and tributyl O-acetylcitrate, of which commercially available products exist.

[(D) Compound Having a Chain Hydrocarbon Moiety and One Bond Selected from the Group Consisting of an Ether Bond (—O—), Carbonyl Bond (—CO—), Ester Bond (—COO—) and Carbonate Bond (—OCOO—) Inserted Between a C—C Single Bond of the Chain Hydrocarbon Moiety]

The (D) compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety (hereunder also referred to as "compound (D)") may be ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, or ($d_4$) a dialkyl carbonate.

[($d_1$) Ether of an Aliphatic Monohydric Alcohol and an Aliphatic Monohydric Alcohol]

Ethers of an aliphatic monohydric alcohol and an aliphatic monohydric alcohol include compounds having the following formula (19):

$$R^{19}OR^{20} \tag{19}$$

wherein $R^{19}$ and $R^{20}$ each represent a chain hydrocarbon.

The aliphatic monohydric alcohol consisting of the ether (corresponding to $R^{19}OH$ and $R^{20}OH$ in formula (19)) is not particularly restricted so long as the ether satisfies the conditions for the IOB, melting point and water solubility, and for example, it may be one of the aliphatic monohydric alcohols mentioned for "compound (B)".

In an ether of an aliphatic monohydric alcohol and an aliphatic monohydric alcohol, the IOB is 0.50 when the total number of carbon atoms of the aliphatic monohydric alcohols consisting of the ether, i.e., the total number of carbons of the $R^{19}$ and $R^{20}$ portions in formula (19), is 2, and therefore when the total number of carbons of the aliphatic monohydric alcohols consisting of the ether is about 2 or greater, this condition for the IOB is satisfied. However, when the total number of carbons of the aliphatic monohydric alcohols consisting of the ether is about 6, the water solubility is as high as about 2 g, which is problematic from the viewpoint of vapor pressure as well. In order to satisfy the condition of a water solubility of about 0.00-0.05 g, the total number of carbons of the aliphatic monohydric alcohols consisting of the ether is preferably about 8 or greater.

[($d_2$) Dialkyl Ketone]

The dialkyl ketone may be a compound of the following formula (20):

$$R^{21}COR^{22} \tag{20}$$

wherein $R^{21}$ and $R^{22}$ are each an alkyl group.

In a dialkyl ketone, the IOB is 0.54 when the total number of carbon atoms of $R^{21}$ and $R^{22}$ is 5, and therefore this condition for the IOB is satisfied if the total number of carbons is about 5 or greater. However, when the total number of carbons of dialkyl ketone is about 5, the water solubility is as high as about 2 g. Therefore, in order to satisfy the condition of a water solubility of about 0.00-0.05 g, the total number of carbons of dialkyl ketone is preferably about 8 or greater. In consideration of vapor pressure, the number of carbon atoms of dialkyl ketone is preferably about 10 or greater and more preferably about 12 or greater.

If the total number of carbon atoms of dialkyl ketone is about 8, such as in 5-nonanone, for example, the melting point is approximately −50° C. and the vapor pressure is about 230 Pa at 20° C.

The dialkyl ketone may be a commercially available product, or it may be obtained by a known method, such as by oxidation of a secondary alcohol with chromic acid or the like.

[($d_3$) Ester of a Fatty Acid and an Aliphatic Monohydric Alcohol]

Examples of esters of a fatty acid and an aliphatic monohydric alcohol include compounds having the following formula (21):

$$R^{23}COOR^{24} \tag{21}$$

wherein $R^{23}$ and $R^{24}$ each represent a chain hydrocarbon.

Examples of fatty acids consisting of these esters (corresponding to $R^{23}COOH$ in formula (21)) include the fatty acids mentioned for the "($a_1$) an ester of a chain hydrocarbon tetraol and at least one fatty acids", and specifically these include saturated fatty acids and unsaturated fatty acids, with saturated fatty acids being preferred in consideration of the potential for degradation by oxidation and the like. The aliphatic monohydric alcohol consisting of the ester (corresponding to $R^{24}OH$ in formula (21)) may be one of the aliphatic monohydric alcohols mentioned for "compound (B)".

In an ester of such a fatty acid and aliphatic monohydric alcohol, the IOB is 0.60 when the total number of carbon atoms of the fatty acid and aliphatic monohydric alcohol, i.e. the total number of carbon atoms of the $R^{23}C$ and $R^{24}$ portions in formula (21), is 5, and therefore this condition for the IOB is satisfied when the total number of carbon atoms of the $R^{23}C$ and $R^{24}$ portions is about 5 or greater. However, with butyl acetate in which the total number of carbon atoms is 6, the vapor pressure is high at greater than 2,000 Pa. In consideration of vapor pressure, therefore, the total number of carbon atoms is preferably about 12 or greater. If the total number of carbon atoms is about 11 or greater, it will be possible to satisfy the condition of a water solubility of about 0.00-0.05 g.

Examples of esters of such fatty acids and aliphatic monohydric alcohols include esters of dodecanoic acid ($C_{12}$) and dodecyl alcohol ($C_{12}$) and esters of tetradecanoic acid ($C_{14}$) and dodecyl alcohol ($C_{12}$), and examples of commercial products of esters of such fatty acids and aliphatic monohydric alcohols include ELECTOL WE20 and ELECTOL WE40 (both products of NOF Corp.).

[($d_4$) Dialkyl Carbonate]

The dialkyl carbonate may be a compound of the following formula (22):

$$R^{25}OC(=O)OR^{26} \tag{22}$$

wherein $R^{25}$ and $R^{26}$ are each an alkyl group.

In a dialkyl carbonate, the IOB is 0.57 when the total number of carbon atoms of $R^{25}$ and $R^{26}$ is 6, and therefore this condition for the IOB is satisfied if the total number of carbons of $R^{25}$ and $R^{26}$ is about 6 or greater.

In consideration of water solubility, the total number of carbon atoms of $R^{25}$ and $R^{26}$ is preferably about 7 or greater and more preferably about 9 or greater.

The dialkyl carbonate may be a commercially available product, or it may be synthesized by reaction between phosgene and an alcohol, reaction between formic chloride and an alcohol or alcoholate, or reaction between silver carbonate and an alkyl iodide.

[(E) Polyoxy $C_2$-$C_6$ Alkylene Glycol, or Ester or Ether Thereof]

The (E) polyoxy $C_2$-$C_6$ alkylene glycol, or ester or ether thereof (hereunder also referred to as "compound (E)") may be ($e_1$) a polyoxy $C_2$-$C_6$ alkylene glycol, ($e_2$) an ester of a polyoxy $C_2$-$C_6$ alkylene glycol and at least one fatty acid, ($e_3$) an ether of a polyoxy $C_2$-$C_6$ alkylene glycol and at least one aliphatic monohydric alcohol, ($e_4$) an ester of a polyoxy $C_2$-$C_6$ alkylene glycol and a chain hydrocarbon tetracarboxylic acid, chain hydrocarbon tricarboxylic acid or chain hydrocarbon dicarboxylic acid, or ($e_5$) an ether of a polyoxy $C_2$-$C_6$ alkylene glycol and a chain hydrocarbon tetraol, chain hydrocarbon triol or chain hydrocarbon diol. These will now be explained.

[($e_1$) Polyoxy $C_2$-$C_6$ Alkylene Glycol]

Polyoxy $C_2$-$C_6$ alkylene glycols refer to i) one or more homopolymers having a unit selected from the group consisting of oxy $C_2$-$C_6$ alkylene units, such as oxyethylene unit, oxypropylene unit, oxybutylene unit, oxypentylene unit and oxyhexylene unit and having hydroxyl groups at both ends, ii) one or more block copolymers having 2 or more units selected from oxy $C_2$-$C_6$ alkylene units described above and oxyhexylene unit and having hydroxyl groups at both ends, or iii) random copolymers having 2 or more units selected from oxy $C_2$-$C_6$ alkylene units described above and having hydroxyl groups at both ends.

The oxy $C_2$-$C_6$ alkylene units are preferably oxypropylene unit, oxybutylene unit, oxypentylene unit or oxyhexylene unit, and more preferably oxybutylene unit, oxypentylene unit and oxyhexylene unit, from the viewpoint of reducing the value of IOB.

The polyoxy $C_2$-$C_6$ alkylene glycol can be represented by the following formula (23):

$$HO-(C_mH_{2m}O)_n-H \tag{23}$$

wherein m represents an integer of 2-6.

The present inventors have confirmed that in polyethylene glycol (corresponding to the homopolymer of formula (23) where m=2), when n≥45 (the weight-average molecular weight exceeds about 2,000), the condition for IOB of about 0.00 to about 0.60 is satisfied, but the condition for the water solubility is not satisfied even when the weight-average molecular weight exceeds about 4,000. Therefore, ethylene glycol homopolymer is not included in the ($e_1$) polyoxy $C_2$-$C_6$ alkylene glycol, and ethylene glycol is included in the ($e_1$) polyoxy $C_2$-$C_6$ alkylene glycol only as a copolymer or random polymer with another glycol.

Thus, homopolymers of formula (23) may include propylene glycol, butylene glycol, pentylene glycol or hexylene glycol homopolymer.

For this reason, m in formula (23) is about 3 to 6 and preferably about 4 to 6, and n is 2 or greater.

The value of n in formula (23) is a value such that the polyoxy $C_2$-$C_6$ alkylene glycol has an IOB of about 0.00-0.60, a melting point of about 45° C. or less and a water solubility of about 0.00-0.05 g in 100 g of water at 25° C.

For example, when formula (23) is polypropylene glycol (m=3, homopolymer), the IOB is 0.58 when n=12. Thus, when formula (23) is polypropylene glycol (m=3, homopolymer), the condition for the IOB is satisfied when m is equal to or greater than about 12.

Also, when formula (23) is polybutylene glycol (m=4, homopolymer), the IOB is 0.57 when n=7. Thus, when formula (23) is polybutylene glycol (m=4, homopolymer), the condition for the IOB is satisfied when n is equal to or greater than about 7.

From the viewpoint of IOB, melting point and water solubility, the weight-average molecular weight of the polyoxy $C_4$-$C_6$ alkylene glycol is preferably between about 200 and about 10,000, more preferably between about 250 and about 8,000, and even more preferably in the range of about 250 to about 5,000.

Also from the viewpoint of IOB, melting point and water solubility, the weight-average molecular weight of a polyoxy $C_3$ alkylene glycol, i.e. polypropylene glycol, is preferably between about 1,000 and about 10,000, more preferably between about 3,000 and about 8,000, and even more preferably between about 4,000 and about 5,000. This is because if the weight-average molecular weight is less than about 1,000, the condition for the water solubility will not be satisfied, and a larger weight-average molecular weight will particularly tend to increase the migration rate into the absorbent body and the whiteness of the top sheet.

Examples of commercial products of polyoxy $C_2$-$C_6$ alkylene glycols include UNIOL™ D-1000, D-1200, D-2000, D-3000, D-4000, PB-500, PB-700, PB-1000 and PB-2000 (all products of NOF Corp.).

[($e_2$) Ester of a Polyoxy $C_2$-$C_6$ Alkylene Glycol and at Least One Fatty Acid]

Examples of an ester of a polyoxy $C_2$-$C_6$ alkylene glycol and at least one fatty acids include the polyoxy $C_2$-$C_6$ alkylene glycols mentioned for "($e_1$) Polyoxy $C_2$-$C_6$ alkylene glycol" in which one or both OH ends have been esterified with fatty acids, i.e. monoesters and diesters.

Examples of fatty acids to be esterified in the ester of a polyoxy $C_2$-$C_6$ alkylene glycol and at least one fatty acid include the fatty acids mentioned for the "($a_1$) Ester of a chain hydrocarbon tetraol and at least one fatty acid", and specifically these include saturated fatty acids and unsaturated fatty acids, with saturated fatty acids being preferred in consideration of the potential for degradation by oxidation and the like.

An example of a commercially available ester of a polyoxy $C_2$-$C_6$ alkylene glycol and a fatty acid is WILBRITE cp9 (product of NOF Corp.).

[($e_3$) Ether of a Polyoxy $C_2$-$C_6$ Alkylene Glycol and at Least One Aliphatic Monohydric Alcohol]

Examples of an ether of a polyoxy $C_2$-$C_6$ alkylene glycols and at least one aliphatic monohydric alcohol include the polyoxy $C_2$-$C_6$ alkylene glycols mentioned for "($e_1$) Polyoxy $C_2$-$C_6$ alkylene glycol" wherein one or both OH ends have been etherified by an aliphatic monohydric alcohol, i.e. monoethers and diethers.

In an ether of a polyoxy $C_2$-$C_6$ alkylene glycol and at least one aliphatic monohydric alcohol, the aliphatic monohydric alcohol to be etherified may be an aliphatic monohydric alcohol among those mentioned for "compound (B)".

[($e_4$) Ester of a Polyoxy $C_2$-$C_6$ Alkylene Glycol and a Chain Hydrocarbon Tetracarboxylic Acid, Chain Hydrocarbon Tricarboxylic Acid or Chain Hydrocarbon Dicarboxylic Acid]

The polyoxy $C_2$-$C_6$ alkylene glycol to be esterified for the aforementioned ester of a polyoxy $C_2$-$C_6$ alkylene glycol and a chain hydrocarbon tetracarboxylic acid, chain hydrocarbon tricarboxylic acid or chain hydrocarbon dicarboxylic acid may be any of the polyoxy $C_2$-$C_6$ alkylene glycols mentioned above under "($e_1$) Polyoxy $C_2$-$C_6$ alkylene glycol". Also, the chain hydrocarbon tetracarboxylic acid, chain hydrocarbon tricarboxylic acid or chain hydrocarbon dicarboxylic acid to be esterified may be any of those mentioned above for "compound (C)".

The ester of a polyoxy $C_2$-$C_6$ alkylene glycol and a chain hydrocarbon tetracarboxylic acid, chain hydrocarbon tricarboxylic acid or chain hydrocarbon dicarboxylic acid may be a commercially available product, or it may be produced by polycondensation of a $C_2$-$C_6$ alkylene glycol with a chain hydrocarbon tetracarboxylic acid, chain hydrocarbon tricarboxylic acid or chain hydrocarbon dicarboxylic acid under known conditions.

[($e_5$) Ether of a Polyoxy $C_2$-$C_6$ Alkylene Glycol and a Chain Hydrocarbon Tetraol, Chain Hydrocarbon Triol or Chain Hydrocarbon Diol]

The polyoxy $C_2$-$C_6$ alkylene glycol to be etherified for the aforementioned ether of a polyoxy $C_2$-$C_6$ alkylene glycol and a chain hydrocarbon tetraol, chain hydrocarbon triol or chain hydrocarbon diol may be any of the polyoxy $C_2$-$C_6$ alkylene glycols mentioned above under "($e_1$) polyoxy $C_2$-$C_6$ alkylene glycol". Also, the chain hydrocarbon tetraol, chain hydrocarbon triol or chain hydrocarbon diol to be etherified may be, for example, pentaerythritol, glycerin or glycol, mentioned above for "compound (A)".

Examples of commercially available ethers of polyoxy $C_2$-$C_6$ alkylene glycols and chain hydrocarbon tetraols, chain hydrocarbon triols and chain hydrocarbon diols include UNILUBE™ 5TP-300 KB and UNIOL™ TG-3000 and TG-4000 (products of NOF Corp.).

UNILUBE™ 5TP-300 KB is a compound obtained by polycondensation of 65 mol of propylene glycol and 5 mol of ethylene glycol with 1 mol of pentaerythritol, and it has an IOB of 0.39, a melting point of below 45° C., and a water solubility of less than 0.05 g.

UNIOL™ TG-3000 is a compound obtained by polycondensation of 50 mol of propylene glycol with 1 mol of glycerin, and it has an IOB of 0.42, a melting point of below 45° C., a water solubility of less than 0.05 g, and a weight-average molecular weight of about 3,000.

UNIOL™ TG-4000 is a compound obtained by polycondensation of 70 mol of propylene glycol with 1 mol of glycerin, and it has an IOB of 0.40, a melting point of below 45° C., a water solubility of less than 0.05 g, and a weight-average molecular weight of about 4,000.

The ether of a polyoxy $C_2$-$C_6$ alkylene glycol and a chain hydrocarbon tetraol, chain hydrocarbon triol or chain hydrocarbon diol may also be produced by adding a $C_2$-$C_6$ alkylene oxide to a chain hydrocarbon tetraol, chain hydrocarbon triol or chain hydrocarbon diol under known conditions.

[(F) Chain Hydrocarbon]

The chain hydrocarbon has an inorganic value of 0 and thus an IOB of 0.00, while the water solubility is also approximately 0 g, and therefore if the melting point is about 45° C. or less it may be included among the aforementioned blood modifying agents. Examples of such chain hydrocarbons include ($f_1$) a chain alkane, such as linear alkanes and branched alkanes, and linear alkanes generally include those with no more than 22 carbons, in consideration of a melting point of about 45° C. or less. In consideration of vapor pressure, they generally include those with 13 or more carbons. Branched alkanes generally include those with 22 or more carbons, since their melting points are often lower than linear alkanes, given the same number of carbon atoms.

Examples of commercially available hydrocarbon products include PARLEAM 6 (NOF Corp.).

The blood modifying agent has been found to have at least a function of lowering blood viscosity and surface tension, which will be considered in detail in the examples. Menstrual blood to be absorbed by the absorbent article, unlike ordinary blood, contains proteins of the endometrial wall, for example, which act to bind together blood cells so that the blood cells form a rouleau state. Menstrual blood which is to be absorbed by the absorbent article therefore tends to have high viscosity, and when the top sheet and second sheet are nonwoven fabrics or woven fabric, the menstrual blood becomes clogged between the fibers creating a residual sticky feel for the wearer, while the menstrual blood also diffuses on the surface of the top sheet and tends to leak.

In an embodiment in which the domed section comprises a blood modifying agent which is believed to have a mechanism of lowering blood viscosity and surface tension, it is possible to minimize clogging of menstrual blood between the top sheet fibers and inside the cushion section, and to allow rapid migration of menstrual blood from the top sheet to the absorbent body through the cushion section. In particular, the absorbent article of the present disclosure has the cushion section between the top sheet and the absorbent body in the domed section, and therefore the spacing between the top sheet and the absorbent body tends to be greater than in a conventional absorbent article. Consequently, when the domed section comprises a blood modifying agent, blood that has reached the top sheet rapidly migrates into the absorbent body through the cushion section, thus further helping to prevent leakage.

In addition, the blood modifying agent which has an IOB of about 0.00 to 0.60 has high organicity and readily infiltrates between blood cells, and it therefore stabilizes the blood cells and prevents formation of a rouleau structure by the blood cells.

Since the blood modifying agent stabilizes blood cells and helps to prevent formation of a rouleau structure by the blood cells, it facilitates absorption of menstrual blood by the absorbent body. For example, with an absorbent article comprising an acrylic super-absorbent polymer, or SAP, absorption of menstrual blood is known to lead to covering of the SAP surface by rouleau-formed blood cells and inhibition of the absorption performance of the SAP, but stabilization of the blood cells allows the absorption performance of the SAP to be exhibited more easily. In addition, the blood modifying agent which has high affinity with erythrocytes protects the erythrocyte membranes, and therefore minimizes destruction of the erythrocytes.

Any liquid-permeable top sheet that is commonly used in the art may be employed without any particular restrictions, and for example, it may be a sheet-like material having a structure that allows permeation of liquids, such as a porous film, woven fabric, nonwoven fabric or the like. The fibers composing such a woven fabric or nonwoven fabric may be natural fibers or chemical fibers, with examples of natural fibers including cellulose, such as ground pulp and cotton, and examples of chemical fibers including regenerated cellulose, such as rayon and fibril rayon, semi-synthetic cellulose, such as acetate and triacetate, thermoplastic hydrophobic chemical fibers, and hydrophilicized thermoplastic hydrophobic chemical fibers.

Examples of thermoplastic hydrophobic chemical fibers include polyethylene (PE), polypropylene (PP) and polyethylene terephthalate (PET) monofilaments, and fibers including PE and PP graft polymers.

Examples of nonwoven fabrics include air-through nonwoven fabrics, spunbond nonwoven fabrics, point bond nonwoven fabrics, spunlace nonwoven fabrics, needle punching nonwoven fabrics and meltblown nonwoven fabrics, as well as combinations thereof (such as SMS and the like).

Liquid-impermeable back sheets include films comprising PE and PP, air-permeable resin films, air-permeable resin films bonded to spunbond or spunlace nonwoven fabrics, and multilayer nonwoven fabrics, such as SMS. In consideration of flexibility of the absorbent article, a low-density polyethylene (LDPE) film with a basis weight of about 15-30 g/m², for example, is preferred.

The first example of the absorbent body is one having an absorbent core covered with a core wrap.

Examples of components for the absorbent core include hydrophilic fibers, including cellulose, such as ground pulp or cotton, regenerated cellulose, such as rayon or fibril rayon, semi-synthetic cellulose, such as acetate or triacetate, particulate polymers, filamentous polymers, thermoplastic hydrophobic chemical fibers, and hydrophilicized thermoplastic hydrophobic chemical fibers, as well as combinations of the foregoing. The component of the absorbent core may also be a super absorbent polymer, such as granules of a sodium acrylate copolymer or the like.

The core wrap is not particularly restricted so long as it is a substance that is liquid-permeable and with a barrier property that does not allow permeation of the polymer absorber, and it may be a woven fabric or nonwoven fabric, for example. The woven fabric or nonwoven fabric may be made of a natural fiber, chemical fiber, tissue, or the like.

A second example of the absorbent body is one formed from an absorbing sheet or polymer sheet, with a thickness of preferably about 0.3-5.0 mm. The absorbing sheet or polymer sheet may usually be used without any particular restrictions so long as it is one that can be used in an absorbent article, such as a sanitary napkin.

The blood modifying agent may be present at any location in the planar direction of the top sheet, such as across the entire top sheet, or at the center region near the vaginal opening.

In an embodiment in which the domed section comprises a blood modifying agent, when the liquid-permeable top sheet is formed from a nonwoven fabric or woven fabric, the blood modifying agent preferably does not obstruct the voids between the fibers of the nonwoven fabric or woven fabric, and for example, the blood modifying agent may be attached as droplets or particulates on the surface of the nonwoven fabric fibers, or covering the surfaces of the fibers.

On the other hand, in an embodiment in which the domed section comprises a blood modifying agent, when the liquid-permeable top sheet is formed from a porous film, the blood modifying agent preferably does not obstruct the holes in the porous film, and for example, the blood modifying agent may be attached as droplets or particulates on the surface of the porous film. This is because if the blood modifying agent obstructs the voids between the fibers of the nonwoven fabric or woven fabric or the holes in the porous film, migration of the absorbed liquid into the absorbent body may be inhibited.

In an embodiment in which the domed section comprises a blood modifying agent, the blood modifying agent also preferably has a large surface area, in order to allow rapid migration into the absorbed liquid, and a blood modifying agent present as droplets or particulates preferably has a small particle size.

In an embodiment in which the domed section comprises a blood modifying agent, when the material to be coated with the blood modifying agent, such as the top sheet, is a nonwoven fabric or porous film made of a synthetic resin, it is preferably coated with or mixed with a hydrophilic agent for hydrophilicizing treatment. If the original material is hydrophilic, since it is subsequently coated with a lipophilic modifying agent having an IOB of about 0.00-0.60 and high organicity, there will be created sparsely dispersed lipophilic regions and hydrophilic regions. This allows consistent absorption performance to be exhibited for menstrual blood which consists of hydrophilic components (blood plasma, etc.) and lipophilic components (blood cells, etc.).

In an embodiment in which the domed section comprises a blood modifying agent, there are no particular restrictions on the method of coating the blood modifying agent, and coating may be accomplished with heating as necessary, using a non-contact coater, such as for example, a spiral coater, curtain coater, spray coater or dip coater, or a contact coater or the like. A non-contact coater is preferred from the viewpoint of uniformly dispersing the droplet or particulate modifying agent throughout, and from the viewpoint of not causing damage in the material. The blood modifying agent may be coated directly, if it is a liquid at room temperature, or it may be heated to lower the viscosity, and when it is a solid at room temperature, it may be heated to liquefaction and coated through a control seam hot melt adhesive (HMA) gun. By increasing the air pressure of the control seam HMA gun, it is possible to coat the blood modifying agent as fine particulates.

In an embodiment in which the domed section comprises a blood modifying agent, the blood modifying agent may be coated during production of the material for the top sheet and/or second sheet, such as the nonwoven fabric, or it may be coated in the manufacturing line for production of the absorbent article. In an embodiment in which the domed section comprises a blood modifying agent, from the viewpoint of minimizing equipment investment, the blood modifying agent is preferably coated in the manufacturing line for the absorbent article, and in order to prevent shedding of the blood modifying agent which may contaminate the line, the blood modifying agent is preferably coated during a step downstream from the manufacturing line, and specifically, immediately before encapsulation of the product in an individual package.

In an embodiment in which the domed section comprises a blood modifying agent, the blood modifying agent may also have an effect as a lubricant. When the top sheet is a nonwoven fabric, it is possible to reduce friction between fibers, thereby improving the flexibility of the nonwoven fabric as a whole. When the top sheet is a resin film, it is possible to reduce friction between the top sheet and the skin.

In an embodiment in which the domed section comprises a blood modifying agent, the weight-average molecular weight of the blood modifying agent is preferably about 2,000 or less, and more preferably about 1,000 or less. A high weight-average molecular weight will tend to result in high viscosity of the blood modifying agent, and it will be difficult to lower the viscosity of the blood modifying agent by heating, to a viscosity suitable for coating. As a result, it will sometimes be necessary to dilute the blood modifying agent with a solvent. In addition, if the weight-average molecular weight is higher, tack may result in the blood modifying agent itself, tending to create a feeling of unpleasantness for the wearer.

The absorbent article is preferably one intended for absorption of blood, such as a sanitary napkin, panty liner or the like.

EXAMPLES

The disclosure will now be explained by examples, with the understanding that the disclosure is not meant to be limited to the examples.

Production Example 1

As a top sheet there was prepared an air-through nonwoven fabric (basis weight: 30 g/m$^2$) comprising hydrophilicized composite fibers (size: 2.8 dtex) having a core-sheath structure with a polyethylene (PE) sheath and a polyethylene terephthalate (PET) core.

As a cushion section there was prepared an air-through nonwoven fabric (basis weight: 30 g/m$^2$) comprising hydrophilicized composite fibers (size: 2.2 dtex) having a core-sheath structure with a polyethylene (PE) sheath and a polyethylene terephthalate (PET) core. The cushion section before being incorporated into the absorbent article, as shown in FIG. 7(a), had a roughly rounded elliptical shape as the projected form in the thickness direction of the absorbent article, and a constant thickness, while the length in the lengthwise direction was 70 mm and the length in the widthwise direction was 30 mm.

A mixture of pulp and SAP blended at 90:10 (mass ratio) (basis weight: 250 g/m$^2$) was wrapped with tissue (basis weight: 14 g/m$^2$) to form an absorbent body.

As a back sheet there was prepared a film comprising PE (basis weight: 23 g/m$^2$), coated with an adhesive on one side.

The absorbent body, cushion section and top sheet were layered in that order, and the absorbent body and top sheet were embossed as shown in FIGS. 1 to 5, to form a domed section. For formation of the domed section, the outside of the cushion section was embossed but the cushion section itself was not embossed. Next, the absorbent body and back sheet were bonded and cut as shown in FIGS. 1 to 5, to produce absorbent article No. 1-1. For absorbent article No. 1-1, the length in the lengthwise direction of the domed section was approximately 70 mm, and the length in the widthwise direction of the domed section was approximately 35 mm. The length in the lengthwise direction of absorbent article No. 1-1 was approximately 176 mm, and the length in the widthwise direction was approximately 80 mm.

For absorbent article No. 1-1, the work of compression WC and the compressional resilience RC were measured at the center section of the domed section, and more specifically the top part of the domed section. A KES-G5 by Kato Tech Corp. was used for measurement under the test conditions described herein. The results are shown in Table 2 below.

Production Examples 2 to 6

Absorbent articles No. 1-2 to No. 1-6 were produced in the same manner as Production Example 1, except that the type and average basis weight of the material composing the cushion section was changed as shown in Table 2. For absorbent articles No. 1-2 to No. 1-4 the basis weights of the air-through nonwoven fabrics composing the cushion sections were different from absorbent article No. 1-1, while the cushion sections of absorbent articles No. 1-2, No. 1-3 and No. 1-4 were formed by layering 3, 10 and 25 air-through nonwoven fabrics (basis weight: 30 g/m$^2$), respectively, using an adhesive. The cushion sections of absorbent articles No. 1-2, No. 1-3 and No. 1-4 had smaller sizes toward the upper layer air-through nonwoven fabrics, and were formed to have the overall shape shown in FIG. 7(d). The pulp and web used in absorbent articles No. 1-5 and No. 1-6 were formed into the shape shown in FIG. 7(d).

The compressional resilience RC and work of compression WC at the center sections of the domed sections of each of the absorbent articles No. 1-2 to No. 1-6 are shown in Table 2.

Several sheets of absorbent articles No. 1-1 to No. 1-6 were each prepared and worn by several test participants, and the compressibility and recoverability (leakage property) were evaluated based on the following criteria.

Because it is difficult to experience recoverability directly, the recoverability was judged to be sufficient when no leakage was present.

[Compressibility]

G: No noticeable feeling of discomfort due to domed section during wear.

P: Noticeable feeling of discomfort due to domed section during wear.

[Recoverability (Leakage Property)]

G: No leakage during wear.

P: Leakage during wear.

Particularly with absorbent articles No. 1-3 and No. 1-4, the thicknesses of the cushion sections at the center sections of the domed sections were approximately equal to the thicknesses of the cushion sections, but the thicknesses of the cushion sections at the outer peripheral sections of the domed sections were even thinner than the original thicknesses of the cushion sections. For absorbent articles No. 1-3 and No. 1-4, therefore, the densities of the cushion sections at the outer peripheral sections of the domed sections were clearly higher than the densities of the cushion sections at the center sections of the domed sections.

TABLE 2

| Absorbent article No. | Cushion section | | | | | | |
|---|---|---|---|---|---|---|---|
| | Type of cushion section | Average basis weight (g/m$^2$) | Maximum thickness (mm) | WC (N·m/m$^2$) | RC (%) | Compressibility | Recoverability (Leakage) |
| 1-1 | Air-through | 30 | 1.3 | 2.1 | 41 | P | G |
| 1-2 | Air-through | 90 | 3.5 | 13.4 | 48 | G | G |
| 1-3 | Air-through | 300 | 10.7 | 30.1 | 62 | G | G |
| 1-4 | Air-through | 750 | 27.8 | 43.2 | 53 | G | G |
| 1-5 | Pulp | 250 | 11.1 | 8.6 | 24 | P | P |
| 1-6 | Web | 250 | 20.2 | 12.5 | 31 | G | P |

TABLE 3

| Absorbent article No. | Maximum thickness (mm) | Average basis weight (g/m$^2$) | Compressive force (N) | Folding property and recoverability |
|---|---|---|---|---|
| 2-1 | 1.3 | 30 | 0.09 | P$^{a)}$ |
| 2-2 | 3.5 | 90 | 0.21 | F-G |
| 2-3 | 5.7 | 150 | 0.35 | G |
| 2-4 | 10.7 | 300 | 1.46 | G |
| 2-5 | 16.0 | 450 | 1.82 | G |
| 2-6 | 21.9 | 600 | 2.22 | G |
| 2-7 | 27.8 | 750 | 3.56 | F-G |
| 2-8 | 31.5 | 900 | 3.80 | P$^{b)}$ |

$^{a)}$Problem with recoverability.
$^{b)}$Problem with folding property.

Production Examples 7 to 14

Absorbent articles No. 2-1 to No. 2-8 were produced in the same manner as Production Example 1, except that the average basis weight of the air-through nonwoven fabric composing the cushion section was changed as shown in Table 3. The cushion section used for each of Production Examples 7 to 14 was roughly rounded rectangular in a projection drawing in the thickness direction of the absorbent article, and with a constant thickness, as shown in FIG. 7(c).

The compressive force of each of the cushion sections composing absorbent articles No. 2-1 to No. 2-8 was measured by the method described herein. The results are shown in Table 3 below.

The stand (and operating stage) used was an FGS-50X-H digital force gauge stand by Nidec-Shinpo Corp., the digital force gauge used was an FGP-0.5 digital force gauge by Nidec-Shinpo Corp., with the press adapter (square, single-side length: 15 mm) set, and the compression parts used were plastic plates (weight: 38.5 g, diameter: 100 mm, height: 30 mm). When the cushion section was compressed using the apparatus, the center section in the widthwise direction of the cushion section expanded, being deformed outward.

Example 2

Several sheets of absorbent articles No. 2-1 to No. 2-8 were each prepared and worn by several test participants, and the folding property and recoverability of the folded absorbent article was evaluated based on the following criteria.

G: No problems with folding property or recoverability.

P: Problems with folding property and/or recoverability.

The results are shown in Table 3 below.

Production Example 15

PANACET 810s (product of NOF Corp., triester of glycerin and fatty acid) was selected as the blood modifying agent, and the PANACET 810s was coated on the domed section of absorbent article No. 2-4 as the center, from a control seam HMA gun at room temperature, to a basis weight of 5.0 g/m$^2$, to produce absorbent article No. 3-1. With an electron microscope it was confirmed that the PANACET 810s was adhering as fine particulates onto the surfaces of the fibers of the top sheet of the domed section.

Example 3

Absorbent article No. 2-4 was worn by 10 test participants and the responses for a total of 20 tests indicated a low area of surface contamination and low leakage. In addition, the responses indicated excellent deformation following movement of the legs, and therefore an excellent fitting property between the domed section and labia minora, both when dry and when wet.

Next, absorbent article No. 3-1 was worn by 10 test participants, and the responses from 20 tests indicated that the area of surface contamination was low and leakage was low compared to absorbent article No. 2-4.

Example 4

Additional Blood Modifying Agent Data

A commercially available sanitary napkin was prepared. The sanitary napkin was formed from a top sheet, formed of a hydrophilic agent-treated air-through nonwoven fabric (composite fiber composed of polyester and polyethylene terephthalate, basis weight: 35 g/m$^2$), a second sheet, formed of an air-through nonwoven fabric (composite fiber composed of polyester and polyethylene terephthalate, basis weight: 30 g/m²), an absorbent body comprising pulp (basis weight: 150-450 g/m², increased at the center section), an acrylic super-absorbent polymer (basis weight: 15 g/m²) and tissue as a core wrap, a water-repellent agent-treated side sheet, and a back sheet composed of a polyethylene film.

The blood modifying agents used for testing are listed below.

[($a_1$) Ester of a Chain Hydrocarbon Tetraols and at Least One Fatty Acid]

UNISTAR H-408BRS, product of NOF Corp.

Pentaerythritol tetra(2-ethylhexanoate), weight-average molecular weight: approximately 640

UNISTAR H-2408BRS-22, product of NOF Corp.

Mixture of pentaerythritol tetra(2-ethylhexanoate) and neopentylglycol di(2-ethylhexanoate) (58:42 as mass ratio), weight-average molecular weight: approximately 520

[($a_2$) Ester of a Chain Hydrocarbon Triols and at Least One Fatty Acid]

Cetiol SB45DEO, Cognis Japan

Glycerin and fatty acid triester, with oleic acid or stearylic acid as the fatty acid.

SOY42, product of NOF Corp.

Glycerin and fatty acid triester with $C_{14}$ fatty acid:$C_{16}$ fatty acid:$C_{18}$ fatty acid:$C_{20}$ fatty acid (including both saturated fatty acids and unsaturated fatty acids) at a mass ratio of about 0.2:11:88:0.8, weight-average molecular weight: 880

Tri-C2L oil fatty acid glyceride, product of NOF Corp.

Glycerin and fatty acid triester with $C_8$ fatty acid:$C_{10}$ fatty acid:$C_{12}$ fatty acid at a mass ratio of about 37:7:56, weight-average molecular weight: approximately 570

Tri-CL oil fatty acid glyceride, product of NOF Corp.

Glycerin and fatty acid triester with $C_8$ fatty acid:$C_{12}$ fatty acid at a mass ratio of about 44:56, weight-average molecular weight: approximately 570

PANACET 810s, product of NOF Corp.

Glycerin and fatty acid triester with $C_8$ fatty acid:$C_{10}$ fatty acid at a mass ratio of about 85:15, weight-average molecular weight: approximately 480

PANACET 800, product of NOF Corp.

Glycerin and fatty acid triester with octanoic acid ($C_8$) as the entire fatty acid portion, weight-average molecular weight: approximately 470

PANACET 800B, product of NOF Corp.

Glycerin and fatty acid triester with 2-ethylhexanoic acid ($C_8$) as the entire fatty acid portion, weight-average molecular weight: approximately 470

NA36, product of NOF Corp.

Glycerin and fatty acid triester with $C_{16}$ fatty acid:$C_{18}$ fatty acid:$C_{20}$ fatty acid (including both saturated fatty acids and unsaturated fatty acids) at a mass ratio of about 5:92:3, weight-average molecular weight: approximately 880

Tri-coconut fatty acid glyceride, product of NOF Corp.

Glycerin and fatty acid triester with $C_8$ fatty acid:$C_{10}$ fatty acid:$C_{12}$ fatty acid:$C_{14}$ fatty acid:$C_{16}$ fatty acid (including both saturated fatty acids and unsaturated fatty acids) at a mass ratio of about 4:8:60:25:3, weight-average molecular weight: 670

Caprylic acid diglyceride, product of NOF Corp.

Glycerin and fatty acid diester with octanoic acid as the fatty acid, weight-average molecular weight: approximately 340

[($a_3$) Ester of a Chain Hydrocarbon Diol and at Least One Fatty Acid]

COMPOL BL, product of NOF Corp.

Dodecanoic acid ($C_{12}$) monoester of butylene glycol, weight-average molecular weight: approximately 270

COMPOL BS, product of NOF Corp.

Octadecanoic acid ($C_{18}$) monoester of butylene glycol, weight-average molecular weight: approximately 350

UNISTAR H-208BRS, product of NOF Corp.

Neopentyl glycol di(2-ethylhexanoate), weight-average molecular weight: approximately 360

[($c_2$) Ester of a Chain Hydrocarbon Tricarboxylic Acid, Hydroxy Acid, Alkoxy Acid or Oxoacid with 3 Carboxyl Groups, and at Least One Aliphatic Monohydric Alcohol]

Tributyl O-acetylcitrate, product of Tokyo Kasei Kogyo Co., Ltd.

Weight-average molecular weight: approximately 400

[($c_3$) Ester of a Chain Hydrocarbon Dicarboxylic Acid, Hydroxy Acid, Alkoxy Acid or Oxoacid with 2 Carboxyl Groups, and at Least One Aliphatic Monohydric Alcohol]

Dioctyl adipate, product of Wako Pure Chemical Industries, Ltd.

Weight-average molecular weight: approximately 380

[($d_3$) Ester of a Fatty Acid and an Aliphatic Monohydric Alcohol]

ELECTOL WE20, product of NOF Corp.

Ester of dodecanoic acid ($C_{12}$) and dodecyl alcohol ($C_{12}$), weight-average molecular weight: approximately 360

ELECTOL WE40, product of NOF Corp.

Ester of tetradecanoic acid ($C_{14}$) and dodecyl alcohol ($C_{12}$), weight-average molecular weight: approximately 390

[($e_1$) Polyoxy $C_2$-$C_6$ Alkylene Glycol]

UNIOL D-1000, product of NOF Corp.

Polypropylene glycol, weight-average molecular weight: approximately 1,000

UNIOL D-1200, product of NOF Corp.

Polypropylene glycol, weight-average molecular weight: approximately 1,200

UNIOL D-3000, product of NOF Corp.

Polypropylene glycol, weight-average molecular weight: approximately 3,000

UNIOL D-4000, product of NOF Corp.

Polypropylene glycol, weight-average molecular weight: approximately 4,000

UNIOL PB500, product of NOF Corp.

Polybutylene glycol, weight-average molecular weight: approximately 500

UNIOL PB700, product of NOF Corp.

Polyoxybutylene polyoxypropylene glycol, weight-average molecular weight: approximately 700

UNIOL PB1000R, product of NOF Corp.

Polybutylene glycol, weight-average molecular weight: approximately 1000

[($e_2$) Ester of a Polyoxy $C_2$-$C_6$ Alkylene Glycol and at Least One Fatty Acid]

WILBRITE cp9, product of NOF Corp.

Polybutylene glycol compound with OH groups at both ends esterified by hexadecanoic acid ($C_{16}$), weight-average molecular weight: approximately 1,150

[($e_3$) Ether of a Polyoxy $C_2$-$C_6$ Alkylene Glycol and at Least One Aliphatic Monohydric Alcohol]

UNILUBE MS-70K, product of NOF Corp.

Stearyl ether of polypropylene glycol, approximately 15 repeating units, weight-average molecular weight: approximately 1,140

[($e_5$) Ethers of a Polyoxy $C_2$-$C_6$ Alkylene Glycol and a Chain Hydrocarbon Tetraol, Chain Hydrocarbon Triol or Chain Hydrocarbon Diol]

UNILUBE 5TP-300 KB

Polyoxyethylenepolyoxypropylene pentaerythritol ether, produced by addition of 5 mol of ethylene oxide and 65 mol of propylene oxide to 1 mol of pentaerythritol, weight-average molecular weight: 4,130

UNIOL TG-3000, product of NOF Corp.

Glyceryl ether of polypropylene glycol, approximately 16 repeating units, weight-average molecular weight: approximately 3,000

UNIOL TG-4000, product of NOF Corp.

Glyceryl ether of polypropylene glycol, approximately 16 repeating units, weight-average molecular weight: approximately 4,000

[($f_1$) Chain Alkane]

PARLEAM 6, product of NOF Corp.

Branched chain hydrocarbon, produced by copolymerization of liquid isoparaffin, isobutene and n-butene followed by hydrogen addition, polymerization degree: approximately 5-10, weight-average molecular weight: approximately 330

[Other Materials]

NA50, product of NOF Corp.

Glycerin and fatty acid triester obtained by addition of hydrogen to NA36 for reduced proportion of double bonds from unsaturated fatty acid starting material, weight-average molecular weight: approximately 880

(Caprylic acid/capric acid) monoglyceride, product of NOF Corp.

Glycerin and fatty acid monoester, with octanoic acid ($C_8$) and decanoic acid ($C_{10}$) at a mass ratio of about 85:15, weight-average molecular weight: approximately 220

Monomuls 90-L2 lauric acid monoglyceride, product of Cognis Japan

Isopropyl citrate, product of Tokyo Kasei Kogyo Co., Ltd.

Weight-average molecular weight: approximately 230

Diisostearyl malate

Weight-average molecular weight: approximately 640

UNIOL D-400, product of NOF Corp.

Polypropylene glycol, weight-average molecular weight: approximately 400

PEG1500, product of NOF Corp.

Polyethylene glycol, weight-average molecular weight: approximately 1,500-1,600

NONION S-6, product of NOF Corp.

Polyoxyethylene monostearate, approximately 7 repeating units, weight-average molecular weight: approximately 880

WILBRITE s753, product of NOF Corp.

Polyoxyethylene polyoxypropylene polyoxybutylene glycerin, weight-average molecular weight: approximately 960

UNIOL TG-330, product of NOF Corp.

Glyceryl ether of polypropylene glycol, approximately 6 repeating units, weight-average molecular weight: approximately 330

UNIOL TG-1000, product of NOF Corp.

Glyceryl ether of polypropylene glycol, approximately 16 repeating units, weight-average molecular weight: approximately 1,000

UNILUBE DGP-700, product of NOF Corp.

Diglyceryl ether of polypropylene glycol, approximately 9 repeating units, weight-average molecular weight: approximately 700

UNIOX HC60, product of NOF Corp.

Polyoxyethylene hydrogenated castor oil, weight-average molecular weight: approximately 3,570

Vaseline, product of Cognis Japan

Petroleum-derived hydrocarbon, semi-solid

The IOBs, melting points and water solubilities of the samples are shown in Table 4.

The water solubility was measured by the method described above, and samples that dissolved 24 hours after addition of 20.0 g to 100 g of desalted water were evaluated as "20 g<", and samples of which 0.05 g dissolved in 100 g of desalted water but 1.00 g did not dissolve were evaluated as 0.05-1.00 g.

For the melting point, "<45" indicates a melting point of below 45° C.

The skin contact surface of the top sheet of the sanitary napkin was coated with the aforementioned blood modifying agent. Each blood modifying agent was used directly, when the blood modifying agent was liquid at room temperature, or when the blood modifying agent was solid at room temperature it was heated to its melting point +20° C., and a control seam HMA gun was used for atomization of the blood modifying agent and coating onto the entire skin contact surface of the top sheet to a basis weight of about 5 g/m².

Figure 8:
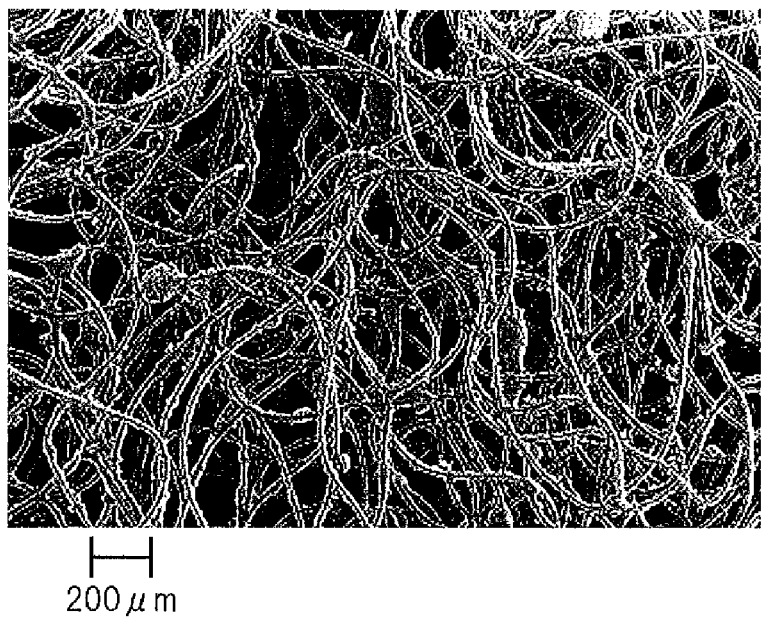
FIG. 8 is an electron micrograph of the skin contact surface of a top sheet in a sanitary napkin wherein the top sheet comprises tri-C2L oil fatty acid glycerides.

FIG. 8 is an electron micrograph of the skin contact surface of a top sheet in a sanitary napkin (No. 3-5) wherein the top sheet comprises tri-C2L oil fatty acid glycerides. As clearly seen in FIG. 8, the tri-C2L oil fatty acid glycerides are adhering onto the fiber surfaces as fine particulates.

[Test Methods]

An acrylic board with an opened hole (200 mm×100 mm, 125 g, with a 40 mm×10 mm hole opened at the center) was placed on a top sheet comprising each blood modifying agent, and 3.0 g of horse EDTA blood at 37±1° C. (obtained by adding ethylenediaminetetraacetic acid (hereunder, "EDTA") to horse blood to prevent coagulation) was dropped through the hole using a pipette (once), and after 1 minute, 3.0 g of horse EDTA blood at 37±1° C. was again added dropwise through the acrylic board hole with a pipette (twice).

After the second dropping of blood, the acrylic board was immediately removed and 10 sheets of filter paper (Advantec Toyo Kaisha, Ltd, Qualitative Filter Paper No. 2, 50 mm×35 mm) were placed on the location where the blood had been dropped, and then a weight was placed thereover to a pressure of 30 g/cm². After 1 minute, the filter paper was removed, and the "rewetting rate" was calculated by the following formula.

Rewetting rate(%)=100×(filter paper mass after test–initial filter paper mass)/6

In addition to the rewetting rate evaluation, the "absorbent body migration rate" was also measured as the time until migration of blood from the top sheet to the absorbent body after the second dropping of blood. The absorbent body migration rate is the time from introducing the blood onto the top sheet, until the redness of the blood could be seen on the surface and in the interior of the top sheet.

The results for the rewetting rate and absorbent body migration rate are shown below in Table 4.

The whiteness of the skin contact surface of the top sheet after the absorbent body migration rate test was visually evaluated on the following scale.

VG (Very Good): Virtually no redness of blood remaining, and no clear delineation between areas with and without blood.

G (Good): Slight redness of blood remaining, but difficult to delineate between areas with and without blood.

F (Fair): Slight redness of blood remaining, areas with blood discernible.

P (Poor): Redness of blood completely remaining.

The results are summarized in Table 4.

TABLE 4

| No. | Type | Blood modifying agent Product name | IOB | Melting pt. (° C.) | Water solubility (g) | Weight-average mol. wt. | Rewetting rate (%) | Absorbent body migration rate (sec) | Top sheet whiteness |
|---|---|---|---|---|---|---|---|---|---|
| 4-1 | (a$_1$) | H-408BRS | 0.13 | <−5 | <0.05 | 640 | 1.2 | 3 | VG |
| 4-2 | | H-2408BRS-22 | 0.18 | <−5 | <0.05 | 520 | 2.0 | 3 | VG |
| 4-3 | (a$_2$) | Cetiol SB45DEO | 0.16 | 44 | <0.05 | | 7.0 | 6 | VG |
| 4-4 | | SOY42 | 0.16 | 43 | <0.05 | 880 | 5.8 | 8 | VG |
| 4-5 | | Tri C2L oil fatty acid glyceride | 0.27 | 37 | <0.05 | 570 | 0.3 | 3 | VG |
| 4-6 | | Tri CL oil fatty acid glyceride | 0.28 | 38 | <0.05 | 570 | 1.7 | 3 | VG |
| 4-7 | | PANACET 810s | 0.32 | −5 | <0.05 | 480 | 2.8 | 3 | VG |
| 4-8 | | PANACET 800 | 0.33 | −5 | <0.05 | 470 | 0.3 | 3 | VG |
| 4-9 | | PANACET 800B | 0.33 | −5 | <0.05 | 470 | 2.0 | 3 | VG |
| 4-10 | | NA36 | 0.16 | 37 | <0.05 | 880 | 3.9 | 5 | VG |
| 4-11 | | Tri-coconut fatty acid glyceride | 0.28 | 30 | <0.05 | 670 | 4.3 | 5 | VG |
| 4-12 | | Caprylic diglyceride | 0.58 | <45 | <0.05 | 340 | 4.2 | 9 | G |
| 4-13 | (a$_3$) | COMPOL BL | 0.50 | 2 | <0.05 | 270 | 2.0 | 5 | G |
| 4-14 | | COMPOL BS | 0.36 | 37 | <0.05 | 350 | 7.9 | 9 | G |
| 4-15 | | H-208BRS | 0.24 | <−5 | <0.05 | 360 | 2.0 | 5 | VG |
| 4-16 | (c$_2$) | Tributyl O-acetylcitrate | 0.60 | <45 | <0.05 | 400 | 6.2 | 8 | VG |
| 4-17 | (c$_3$) | Dioctyl adipate | 0.27 | <45 | <0.05 | 380 | 1.7 | 6 | VG |
| 4-18 | (d$_3$) | ELECTOL WE20 | 0.13 | 29 | <0.05 | 360 | 1.8 | 5 | VG |
| 4-19 | | ELECTOL WE40 | 0.12 | 37 | <0.05 | 390 | 1.8 | 4 | VG |
| 4-20 | (e$_1$) | UNIOL D-1000 | 0.51 | <45 | <0.05 | 1,000 | 6.8 | 15 | F |
| 4-21 | | UNIOL D-1200 | 0.48 | <45 | <0.05 | 1,160 | 0.5 | 11 | F |
| 4-22 | | UNIOL D-3000 | 0.39 | <45 | <0.05 | 3,000 | 1.7 | 10 | F |
| 4-23 | | UNIOL D-4000 | 0.38 | <45 | <0.05 | 4,000 | 1.0 | 7 | G |
| 4-24 | (e$_1$) | UNIOL PB500 | 0.44 | <45 | <0.05 | 500 | 4.5 | 4 | G |
| 4-25 | | UNIOL PB700 | 0.49 | −5 | <0.05 | 700 | 2.8 | 5 | G |
| 4-26 | | UNIOL PB1000R | 0.40 | <45 | <0.05 | 1,000 | 4.0 | 4 | G |
| 4-27 | (e$_2$) | WILBRITE cp9 | 0.21 | 35 | <0.05 | 1,150 | 1.4 | 3 | G |
| 4-28 | (e$_3$) | UNILUBE MS-70K | 0.30 | <−10 | <0.05 | 1,140 | 6.7 | 3 | G |
| 4-29 | (e$_5$) | UNILUBE 5TP-300KB | 0.39 | <45 | <0.05 | 4,130 | 2.0 | 6 | G |
| 4-30 | | UNIOL TG-3000 | 0.42 | <45 | <0.05 | 3,000 | 0.8 | 6 | G |
| 4-31 | | UNIOL TG-4000 | 0.40 | <45 | <0.05 | 4,000 | 2.0 | 6 | G |
| 4-32 | (f$_1$) | PARLEAM 6 | 0.00 | −5 | <0.05 | 330 | 6.0 | 8 | VG |
| 4-33 | | NA50 | 0.18 | 52 | <0.05 | 880 | 15.5 | 60 | P |
| 4-34 | | (Caprylic/capric) monoglyceride | 1.15 | <45 | 20< | 220 | 4.0 | 4 | P |
| 4-35 | | 90-L2 Lauric acid monoglyceride | 0.87 | 58 | 20< | | 6.2 | 7 | P |
| 4-36 | | Isopropyl citrate | 1.56 | <45 | 20< | 230 | 12.2 | 5 | G |
| 4-37 | | Diisostearyl malate | 0.28 | <45 | 20< | 640 | 5.5 | 8 | F |
| 4-38 | | UNIOL D-400 | 0.76 | <45 | 0.05< | 400 | 8.7 | 40 | P |
| 4-39 | | PEG1500 | 0.78 | 40 | 20< | 1,500-1,600 | 11.0 | 38 | P |
| 4-40 | | NONION S-6 | 0.44 | 37 | 0.05< | 880 | 8.4 | 7 | P |
| 4-41 | | WILBRITE s753 | 0.67 | −5 | 20< | 960 | 9.3 | 9 | F |
| 4-42 | | UNIOL TG-330 | 1.27 | <45 | 0.05< | 330 | — | — | — |
| 4-43 | | UNIOL TG-1000 | 0.61 | <45 | <0.05 | 1,000 | 14.2 | 7 | G |
| 4-44 | | UNILUBE DGP-700 | 0.91 | <0 | 0.05< | 700 | — | — | — |
| 4-45 | | UNIOX HC60 | 0.46 | 33 | 0.05-1.00 | 3,570 | 14.6 | 46 | P |
| 4-46 | | Vaseline | 0.00 | 55 | <0.05 | | 9.7 | 10 | F |
| 4-47 | | None | — | — | — | — | 22.7 | 60< | P |

In the absence of a blood modifying agent, the rewetting rate was 22.7% and the absorbent body migration rate was greater than 60 seconds, but the glycerin and fatty acid triesters all produced rewetting rates of 7.0% or less and absorbent body migration rates of no longer than 8 seconds, and therefore significantly improved the absorption performance. Of the glycerin and fatty acid triesters, however, no great improvement in absorption performance was seen with NA50 which had a melting point of above 45° C.

Similarly, the absorption performance was also significantly improved with blood modifying agents having an IOB of about 0.00-0.60, a melting point of about 45° C. or less, and a water solubility of about 0.00-0.05 g in 100 g of water at 25° C.

Next, several volunteer subjects were asked to wear sanitary napkins Nos. 4-1 to 4-47, and the obtained responses indicated that with the sanitary napkins comprising blood modifying agents Nos. 4-1 to 4-32, the top sheets had no sticky feel and the top sheets were smooth, even after absorption of menstrual blood.

Also, with sanitary napkins No. 4-1 to No. 4-32, and particularly with sanitary napkins that comprised blood modifying agents Nos. 4-1 to 11, 15 to 19 and 32, the skin contact surfaces of the top sheets after absorption of menstrual blood had not been reddened by the blood and the unpleasantness was minimal.

Example 4 is a case in which the sanitary napkin did not have the prescribed domed section, and since sanitary napkins No. 4-1 to No. 4-32 had the same results as No. 4-7 which contained PANACET 810s, this suggests that the same result would be obtained as with absorbent article No. 3-1 which was coated with a blood modifying agent (PANACET 810s), if the blood modifying agents used in sanitary napkins No.

4-1 to No. 4-32 are coated onto absorbent article No. 2-4 which was not coated with a blood modifying agent.

Example 5

The rewetting rate was evaluated for blood from different animals, by the procedure described above. The following blood was used for the test.
[Animal Species]
(1) Human
(2) Horse
(3) Sheep
[Types of Blood]
Defibrinated blood: blood sampled and agitated together with glass beads in an Erlenmeyer flask for approximately 5 minutes.

EDTA blood: 65 mL of venous blood with addition of 0.5 mL of a 12% EDTA•2K isotonic sodium chloride solution.
[Fractionation]
Serum or blood plasma: Supernatant obtained after centrifugation of defibrinated blood or EDTA blood for 10 minutes at room temperature at about 1900 G.

Blood cells: Obtained by removing the serum from the blood, washing twice with phosphate buffered saline (PBS), and adding phosphate buffered saline to the removed serum portion.

An absorbent article was produced in the same manner as Example 4, except that the tri-C2L oil fatty acid glyceride was coated at a basis weight of about 5 g/m$^2$, and the rewetting rate of each of the aforementioned blood samples was evaluated. Measurement was performed 3 times for each blood sample, and the average value was recorded.

The results are shown in Table 5 below.

TABLE 5

| | | | Rewetting rate (%) | |
|---|---|---|---|---|
| No. | Animal species | Type of blood | With blood modifying agent | Without blood modifying agent |
| 5-1 | Human | Defibrinated blood | 1.6 | 5.0 |
| 5-2 | | Defibrinated serum | 0.2 | 2.6 |
| 5-3 | | Defibrinated blood cells | 0.2 | 1.8 |
| 5-4 | | EDTA blood | 2.6 | 10.4 |
| 5-5 | | EDTA plasma | 0.0 | 5.8 |
| 5-6 | | EDTA blood cells | 0.2 | 4.3 |
| 5-7 | Horse | Defibrinated blood | 0.0 | 8.6 |
| 5-8 | | Defibrinated serum | 0.2 | 4.2 |
| 5-9 | | Defibrinated blood cells | 0.2 | 1.0 |
| 5-10 | | EDTA blood | 6.0 | 15.7 |
| 5-11 | | EDTA plasma | 0.1 | 9.0 |
| 5-12 | | EDTA blood cells | 0.1 | 1.8 |
| 5-13 | Sheep | Defibrinated blood | 0.2 | 5.4 |
| 5-14 | | Defibrinated serum | 0.3 | 1.2 |
| 5-15 | | Defibrinated blood cells | 0.1 | 1.1 |
| 5-16 | | EDTA blood | 2.9 | 8.9 |
| 5-17 | | EDTA plasma | 0.0 | 4.9 |
| 5-18 | | EDTA blood cells | 0.2 | 1.6 |

The same trend was seen with human and sheep blood as with the horse EDTA blood, as obtained in Example 4. A similar trend was also observed with defibrinated blood and EDTA blood.

Example 6

Evaluation of Blood Retention

The blood retention was evaluated for a top sheet comprising a blood modifying agent and a top sheet comprising no blood modifying agent.
[Test Methods]
(1) A tri-C2L oil fatty acid glyceride was atomized on the skin contact surface of a top sheet formed from an air-through nonwoven fabric (composite fiber composed of polyester and polyethylene terephthalate, basis weight: 35 g/m$^2$), using a control seam HMA gun, for coating to a basis weight of about 5 g/m$^2$. For comparison, there was also prepared a sheet without coating with the tri-C2L oil fatty acid glyceride. Next, both the tri-C2L oil fatty acid glyceride-coated top sheet and the non-coated top sheet were cut to a size of 0.2 g, and the mass (a) of the cell strainer+top sheet was precisely measured.

(2) After adding about 2 mL of horse EDTA blood from the skin contact surface side, it was allowed to stand for 1 minute.

(3) The cell strainer was set in a centrifuge tube, and subjected to spin-down to remove the excess horse EDTA blood.

(4) The mass (b) of the top sheet containing the cell strainer+horse EDTA blood was measured.

(5) The initial absorption (g) per 1 g of top sheet was calculated by the following formula.

$$\text{Initial absorption}(g) = [\text{mass}(b) - \text{mass}(a)]/0.2$$

(6) The cell strainer was again set in the centrifuge tube and centrifuged at room temperature for 1 minute at approximately 1,200 G.

(7) The mass (c) of the top sheet containing the cell strainer+horse EDTA blood was measured.

(8) The post-test absorption (g) per 1 g of top sheet was calculated by the following formula.

$$\text{Post-test absorption} = [\text{mass}(c) - \text{mass}(a)]/0.2$$

(9) The blood retention (%) was calculated according to the following formula.

$$\text{Blood retention}(\%) = 100 \times \text{post-test absorption}(g)/\text{initial absorption}(g)$$

The measurement was conducted 3 times, and the average value was recorded.

The results are shown in Table 6 below.

TABLE 6

| | Blood retention (%) | |
|---|---|---|
| | With blood modifying agent | Without blood modifying agent |
| Horse EDTA blood | 3.3 | 9.2 |

The top sheets comprising blood modifying agents had low blood retentions, suggesting that blood rapidly migrated into the absorbent body after absorption.

Example 7

Viscosity of Blood Containing Blood Modifying Agent

The viscosity of the blood modifying agent-containing blood was measured using a Rheometric Expansion System ARES (Rheometric Scientific, Inc.). After adding 2 mass % of PANACET 810s to horse defibrinated blood, the mixture was gently agitated to form a sample, the sample was placed on a 50 mm-diameter parallel plate, with a gap of 100 μm, and the viscosity was measured at 37±0.5° C. The sample was not subjected to a uniform shear rate due to the parallel plate, but the average shear rate indicated by the device was 10 s$^{-1}$.

The viscosity of the horse defibrinated blood containing 2 mass % PANACET 810s was 5.9 mPa·s, while the viscosity of the horse defibrinated blood containing no blood modifying agent was 50.4 mPa·s. Thus, the horse defibrinated blood containing 2 mass % PANACET 810s clearly had an approximately 90% lower viscosity than the blood containing no blood modifying agent.

It is known that blood contains components, such as blood cells and has thixotropy, and the blood modifying agent of this disclosure lowers blood viscosity in the low viscosity range. Lowering the blood viscosity allows absorbed menstrual blood to rapidly migrate from the top sheet to the absorbent body.

Example 8

Photomicrograph of Blood Modifying Agent-Containing Blood

Menstrual blood was sampled from healthy volunteers onto thin plastic wrap, and PANACET 810s dispersed in a 10-fold mass of phosphate-buffered saline was added to a portion thereof to a PANACET 810s concentration of 1 mass %. The menstrual blood was dropped onto a slide glass, a cover glass was placed thereover, and the state of the erythrocytes was observed with an optical microscope. A photomicrograph of menstrual blood containing no blood modifying agent is shown in FIG. 9(a), and a photomicrograph of menstrual blood containing PANACET 810s is shown in FIG. 9(b).

From FIG. 9(a) and FIG. 9(b), it is seen that the erythrocytes formed aggregates, such as rouleaux in the menstrual blood containing no blood modifying agent, while the erythrocytes were stably dispersed in the menstrual blood containing PANACET 810s. This suggests that the blood modifying agent functions to stabilize erythrocytes in blood.

Example 9

Surface Tension of Blood Containing Blood Modifying Agent

The surface tension of blood containing a blood modifying agent was measured by the pendant drop method, using a Drop Master500 contact angle meter by Kyowa Interface Science Co., Ltd. The surface tension was measured after adding a prescribed amount of blood modifying agent to sheep defibrinated blood, and thoroughly shaking.

Figure 10:
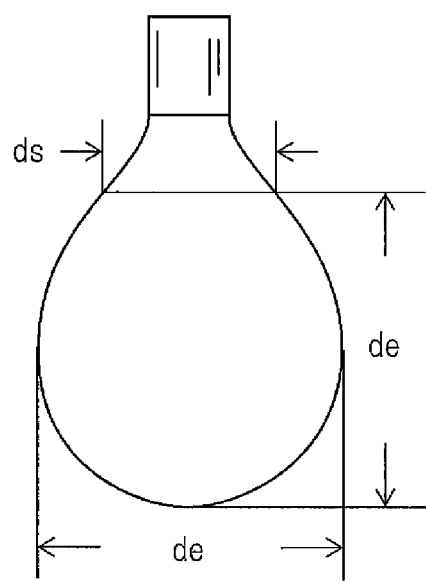
FIG. 10 is a diagram illustrating a method of measuring surface tension.

The measurement was accomplished automatically with a device, and the surface tension γ was determined by the following formula (see FIG. 10).

$$\gamma = g \times \rho \times (de)^2 \times 1/H$$

g: Gravitational constant
1/H: Correction factor determined from ds/de
ρ: Density
de: Maximum diameter
ds: Diameter at location of increase by de from dropping edge The density ρ was measured at the temperatures listed in Table 7, according to JIS K 2249-1995, "Density test methods and density/mass/volume conversion tables", "5. Vibrating density test method".

The measurement was accomplished using a DA-505 by Kyoto Electronics Co., Ltd.

The results are shown in Table 7 below.

TABLE 7

| No. | Blood modifying agent Type | Amount (mass %) | Measuring temperature (° C.) | Surface tension (mN/m) |
|---|---|---|---|---|
| 9-1 | — | — | 35 | 62.1 |
| 9-2 | PANACET | 0.01 | 35 | 61.5 |
| 9-3 | 810s | 0.05 | 35 | 58.2 |
| 9-4 | | 0.10 | 35 | 51.2 |
| 9-5 | ELECTOL WE20 | 0.10 | 35 | 58.8 |
| 9-6 | PARLEAM 6 | 0.10 | 35 | 57.5 |
| 9-7 | — | — | 50 | 56.3 |
| 9-8 | WILBRITE cp9 | 0.10 | 50 | 49.1 |

Table 7 shows that the blood modifying agent can lower the surface tension of blood despite its very low solubility in water, as seen by a water solubility of about 0.00-0.05 g in 100 g of water at 25° C.

Lowering the surface tension of blood allows absorbed blood to rapidly migrate from the top sheet to the absorbent body, without being retained between the top sheet fibers.

The present disclosure relates to the following J1 to J15.

[J1]

An absorbent article comprising a liquid-permeable top sheet, a liquid-impermeable back sheet and an absorbent body between the liquid-permeable top sheet and liquid-impermeable back sheet, wherein the absorbent article has in the excretory opening contact region a domed section that protrudes in the thickness direction of the absorbent article, the domed section comprises part of the top sheet and a cushion section disposed between the top sheet and the absorbent body, and has a center section and an outer peripheral section surrounding the center section, the cushion section has a maximum thickness of 3 to 30 mm, the domed section has a work of compression WC of 10-50 (N·m/m$^2$) and a compressional resilience RC of 35-100% at the center section, and the absorbent body has a length of 80 to 230 mm in the lengthwise direction of the absorbent article and a length of 30 to 90 mm in the widthwise direction of the absorbent article.

[J2]

The absorbent article according to J1, wherein the cushion section has an average basis weight of 50 to 1,000 g/cm$^2$.

[J3]

The absorbent article according to J1 or J2, wherein the cushion section has a compressive force of 0.1-3.6N in the widthwise direction of the absorbent article.

[J4]

The absorbent article according to any one of J1 to J3, wherein the cushion section comprises an air-through non-woven fabric in which the intersections between fibers are heat-fused.

[J5]

The absorbent article according to any one of J1 to J4, wherein the density of the cushion section at the outer peripheral section is higher than the density of the cushion section at the center section.

[J6]

The absorbent article according to any one of J1 to J5, wherein the absorbent article has an embossed section formed by embossing at least the top sheet and the absorbent body, near the outer edge of the cushion section.

[J7]

The absorbent article according to any one of J1 to J6, wherein the cushion section retains at least 50% of its maximum thickness after absorption of 2 g of horse EDTA blood, as compared to before horse EDTA blood absorption.

[J8]

The absorbent article according to any one of J1 to J7, wherein the absorbent article has a curved structure in which the domed section curves inward.

[J9]

The absorbent article according to any one of J1 to J8, wherein the absorbent article has an elastic member at both edges in the lengthwise direction.

[J10]

The absorbent article according to any one of J1 to J9, wherein the top sheet has, on the skin contact surface, a plurality of ridges and a plurality of furrows, extending in the lengthwise direction of the absorbent article.

[J11]

The absorbent article according to any one of J1 to J10, wherein the domed section further comprises a blood modifying agent with an IOB of 0.00-0.60, a melting point of 45° C. or less and a water solubility of 0.00-0.05 g in 100 g of water at 25° C.

[J12]

The absorbent article according to J11, wherein the blood modifying agent is selected from the group consisting of following items (i)-(iii), and any combination thereof:

(i) a hydrocarbon;

(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting for a hydrogen of the hydrocarbon moiety;

with the proviso that when 2 or more oxy groups are inserted in the compound of (ii) or (iii), the oxy groups are not adjacent.

[J13]

The absorbent article according to J11 or J12, wherein the blood modifying agent is selected from the group consisting of following items (i')-(iii'), and any combination thereof:

(i') a hydrocarbon;

(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting for a hydrogen on the hydrocarbon moiety;

with the proviso that when 2 or more same or different bonds are inserted in a compound of (ii') or (iii'), the bonds are not adjacent.

[J14]

The absorbent article according to any one of J11 to J13, wherein the blood modifying agent is selected from the group consisting of following items (A)-(F), and any combination thereof:

(A) an ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety;

(B) an ether of (B1) a compound having a chain hydrocarbon moiety and 2-4 hydroxyl groups substituting for hydrogens on the chain hydrocarbon moiety, and (B2) a compound having a chain hydrocarbon moiety and 1 hydroxyl group substituting for a hydrogen on the chain hydrocarbon moiety;

(C) an ester of (C1) a carboxylic acid, hydroxy acid, alkoxy acid or oxoacid comprising a chain hydrocarbon moiety and 2-4 carboxyl groups substituting for hydrogens on the chain hydrocarbon moiety, and (C2) a compound having a chain hydrocarbon moiety and 1 hydroxyl group substituting for a hydrogen on the chain hydrocarbon moiety;

(D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;

(E) a polyoxy $C_2$-$C_6$ alkylene glycol, or ester or ether thereof; and (F) a chain hydrocarbon.

[J15]

The absorbent article according to any one of J11 to J14, wherein the blood modifying agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_2$-$C_6$ alkylene glycol, ($e_2$) an ester of a polyoxy $C_2$-$C_6$ alkylene glycols and at least one fatty acid, ($e_3$) an ether of a polyoxy $C_2$-$C_6$ alkylene glycol and at least one aliphatic monohydric alcohol, ($e_4$) an ester of a polyoxy $C_2$-$C_6$ alkylene glycols and a chain hydrocarbon tetracarboxylic acid, chain hydrocarbon tricarboxylic acid or chain hydrocarbon dicarboxylic acid, ($e_5$) an ether of a polyoxy $C_2$-$C_6$ alkylene glycol and a chain hydrocarbon tetraol, chain hydrocarbon triol or chain hydrocarbon diol, and ($f_1$) a chain alkane, and any combination thereof.

REFERENCE SIGNS LIST

1 Absorbent article
2 Domed section
3 Embossed section
4 Top sheet
5 Detaching portion
6 Cushion section
7 Absorbent body
8 Back sheet
9 Anchoring part
11 Center section
12 Outer peripheral section
13 Elastic member
21 Compressive force measuring apparatus
22 Stand
23 Operating stage
24 Digital force gauge
25 Sample stage
26 Sample
27 Compression part
28 Stopper

The invention claimed is:

1. An absorbent article comprising a liquid-permeable top sheet, a liquid-impermeable back sheet and an absorbent body between the liquid-permeable top sheet and liquid-impermeable back sheet,
  wherein the absorbent article has in the excretory opening contact region a domed section that protrudes in the thickness direction of the absorbent article,
  the domed section comprises part of the top sheet and a cushion section disposed between the top sheet and the absorbent body, and has a center section and an outer peripheral section surrounding the center section,
  the cushion section has a maximum thickness of 3 to 30 mm,
  the domed section has a work of compression WC of 10-50 (N·m/m$^2$) and a compressional resilience RC of 35-100% at the center section, and
  the absorbent body has a length of 80 to 230 mm in the lengthwise direction of the absorbent article and a length of 30 to 90 mm in the widthwise direction of the absorbent article,
  wherein the cushion section has a compressive force of 0.1-3.6N in the widthwise direction of the absorbent article.

2. The absorbent article according to claim 1, wherein the cushion section has an average basis weight of 50 to 1,000 g/cm$^2$.

3. The absorbent article according to claim 1, wherein the cushion section comprises an air-through nonwoven fabric in which the intersections between fibers are heat-fused.

4. The absorbent article according to claim 1, wherein the density of the cushion section at the outer peripheral section is higher than the density of the cushion section at the center section.

5. The absorbent article according to claim 1, wherein the absorbent article has an embossed section formed by embossing at least the top sheet and the absorbent body, near the outer edge of the cushion section.

6. The absorbent article according to claim 1, wherein the cushion section retains at least 50% of its maximum thickness after absorption of 2 g of horse EDTA blood, as compared to before horse EDTA blood absorption.

7. The absorbent article according to claim 1, wherein the absorbent article has a curved structure in which the domed section curves inward.

8. The absorbent article according to claim 1, wherein the absorbent article has an elastic member at both edges in the lengthwise direction.

9. The absorbent article according to claim 1, wherein the top sheet has, on the skin contact surface, a plurality of ridges and a plurality of furrows, extending in the lengthwise direction of the absorbent article.

10. The absorbent article according to claim 1, wherein the domed section further comprises a blood modifying agent with an IOB of 0.00-0.60, a melting point of 45° C. or less and a water solubility of 0.00-0.05 g in 100 g of water at 25° C.

11. The absorbent article according to claim 10, wherein the blood modifying agent is selected from the group consisting of following items (i)-(iii), and any combination thereof:
  (i) a hydrocarbon;
  (ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and
  (iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting for a hydrogen of the hydrocarbon moiety;
  with the proviso that when 2 or more oxy groups are inserted in the compound of (ii) or (iii), the oxy groups are not adjacent.

12. The absorbent article according to claim 10, wherein the blood modifying agent is selected from the group consisting of following items (i')-(iii'), and any combination thereof:
  (i') a hydrocarbon;
  (ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and
  (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting for a hydrogen on the hydrocarbon moiety;
  with the proviso that when 2 or more same or different bonds are inserted in a compound of (ii') or (iii'), the bonds are not adjacent.

13. The absorbent article according to claim 10, wherein the blood modifying agent is selected from the group consisting of following items (A)-(F), and any combination thereof:
- (A) an ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety;
- (B) an ether of (B1) a compound having a chain hydrocarbon moiety and 2-4 hydroxyl groups substituting for hydrogens on the chain hydrocarbon moiety, and (B2) a compound having a chain hydrocarbon moiety and 1 hydroxyl group substituting for a hydrogen on the chain hydrocarbon moiety;
- (C) an ester of (C1) a carboxylic acid, hydroxy acid, alkoxy acid or oxoacid comprising a chain hydrocarbon moiety and 2-4 carboxyl groups substituting for hydrogens on the chain hydrocarbon moiety, and (C2) a compound having a chain hydrocarbon moiety and 1 hydroxyl group substituting for a hydrogen on the chain hydrocarbon moiety;
- (D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;
- (E) a polyoxy $C_2$-$C_6$ alkylene glycol, or ester or ether thereof; and
- (F) a chain hydrocarbon.

14. The absorbent article according to claim 10, wherein the blood modifying agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_2$-$C_6$ alkylene glycol, ($e_2$) an ester of a polyoxy $C_2$-$C_6$ alkylene glycols and at least one fatty acid, ($e_3$) an ether of a polyoxy $C_2$-$C_6$ alkylene glycol and at least one aliphatic monohydric alcohol, ($e_4$) an ester of a polyoxy $C_2$-$C_6$ alkylene glycols and a chain hydrocarbon tetracarboxylic acid, chain hydrocarbon tricarboxylic acid or chain hydrocarbon dicarboxylic acid, ($e_5$) an ether of a polyoxy $C_2$-$C_6$ alkylene glycol and a chain hydrocarbon tetraol, chain hydrocarbon triol or chain hydrocarbon diol, and ($f_1$) a chain alkane, and any combination thereof.

* * * * *